US011647902B2

(12) United States Patent
Witham et al.

(10) Patent No.: US 11,647,902 B2
(45) Date of Patent: May 16, 2023

(54) OTOSCOPE

(71) Applicants: Nicholas Steven Witham, Salt Lake City, UT (US); Tarek Sami Marrouche, Salt Lake City, UT (US); Allie Kachel, Salt Lake City, UT (US); Bryan R. McRae, Salt Lake City, UT (US)

(72) Inventors: Nicholas Steven Witham, Salt Lake City, UT (US); Tarek Sami Marrouche, Salt Lake City, UT (US); Allie Kachel, Salt Lake City, UT (US); Bryan R. McRae, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/601,014

(22) PCT Filed: Apr. 5, 2020

(86) PCT No.: PCT/US2020/026785
§ 371 (c)(1),
(2) Date: Oct. 1, 2021

(87) PCT Pub. No.: WO2020/206401
PCT Pub. Date: Oct. 8, 2020

(65) Prior Publication Data
US 2022/0095907 A1      Mar. 31, 2022

Related U.S. Application Data

(60) Provisional application No. 62/829,955, filed on Apr. 5, 2019.

(51) Int. Cl.
*A61B 1/06*  (2006.01)
*A61B 1/00*  (2006.01)
(Continued)

(52) U.S. Cl.
CPC ........ *A61B 1/0676* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 4,986,262 A * 1/1991 Saito .................... A61B 1/0661
600/475
5,714,832 A * 2/1998 Shirrod .............. G01B 11/2527
310/330
(Continued)

FOREIGN PATENT DOCUMENTS

KR      101399222 B1      5/2014
WO      2009157825 A1     12/2009

OTHER PUBLICATIONS

Barton, "Otitis Media in Infants and Children", Jama, 2007, vol. 298, No. 19, p. 2313.
(Continued)

*Primary Examiner* — Michael J Carey
*Assistant Examiner* — Minqiao Huang
(74) *Attorney, Agent, or Firm* — Michael Best & Friedrich LLP

(57) ABSTRACT

An otoscope and method for visualizing compliance of the tympanic membrane in response to a pressure stimulus. The otoscope includes a handle, a housing, a laser assembly configured to selectively project a grid array of dots on a tympanic membrane of a patient, a camera configured to
(Continued)

selectively capture activity of the tympanic membrane, a pressure transducer configured to selectively apply a stimulus to the tympanic membrane, a display pivotably coupled to the handle, and a controller. The display is configured to display the tympanic membrane in true color and a two-dimensional interpolated surface plot representing activity of the tympanic membrane in response to the stimulus.

23 Claims, 20 Drawing Sheets

(51) Int. Cl.
  *A61B 1/227* (2006.01)
  *A61B 1/015* (2006.01)
  *A61B 5/12* (2006.01)
(52) U.S. Cl.
  CPC ...... *A61B 1/00052* (2013.01); *A61B 1/00096* (2013.01); *A61B 1/015* (2013.01); *A61B 1/063* (2013.01); *A61B 1/0655* (2022.02); *A61B 1/2275* (2013.01); *A61B 5/12* (2013.01)

(56) References Cited

U.S. PATENT DOCUMENTS

| | | | |
|---|---|---|---|
| 5,847,832 A * | 12/1998 | Liskow | A61B 5/1077 356/613 |
| 5,919,130 A | 7/1999 | Monroe et al. | |
| 7,625,335 B2 * | 12/2009 | Deichmann | G01B 11/25 600/117 |
| 8,647,264 B1 | 2/2014 | Keller | |
| 8,900,126 B2 * | 12/2014 | Bergman | A61B 34/20 600/117 |
| 9,867,528 B1 * | 1/2018 | Boppart | A61B 5/0053 |
| 10,172,513 B2 | 1/2019 | Ruppersberg | |
| 10,213,098 B2 * | 2/2019 | Goldfain | A61B 1/0684 |
| 2003/0171655 A1 | 9/2003 | Newman | |
| 2005/0171399 A1 | 8/2005 | Rich et al. | |
| 2006/0282009 A1 * | 12/2006 | Oberg | A61B 5/0086 600/559 |
| 2012/0310098 A1 * | 12/2012 | Popovic | A61B 5/1076 600/476 |
| 2013/0027515 A1 | 1/2013 | Vinther et al. | |
| 2014/0012141 A1 | 1/2014 | Kim et al. | |
| 2014/0200408 A1 * | 7/2014 | Berglund | A61B 5/1079 600/189 |
| 2018/0168440 A1 | 6/2018 | Das et al. | |
| 2018/0234600 A1 * | 8/2018 | Zeien | A61B 5/0082 |
| 2020/0315499 A1 * | 10/2020 | Adamson | A61B 5/126 |

OTHER PUBLICATIONS

Canadian Patent Office Action for Application No. 3,135,983 dated Nov. 23, 2021 (3 pages).
D'Alessandro, "What Ambient Temperature is Appropriate?", PediatricEducation.org, 2013, <www.pediatriceducation.org/2013/06/03/what-ambient-temperature-is-appropriate/>, 3 pages.
Harmes et al., "Otitis Media: Diagnosis and Treatment,", American Family Physician, 2013, vol. 88, No. 7, pp. 435-440.
Hayes, "What Causes the Accumulation of Fluid in the Ear?", <www.verywellhealth.com/diagnosis-and-treatment-for-fluid-in-the-ear-1192211>, last updated Oct. 2021, 10 pages.
Lanphear et al, "Icreasing Prevalence of Recurrent Otitis Media Among Children in the United States", Pediatrics, vol. 99, No. 3, Mar. 1, 1997, pp. 1-7.
Lee et al., "Clinical Diagnostic Accuracy of Otitis MEdia with Effusion in Children, and Significance of Myringotomy: Diagnostic orTherapeutic?", Journal of Korean Medical Science, 2004, vol. 19, No. 5, pp. 739-743.
Wei et al., "The Efficacy of Myringotomy and Ventilation Tube Insertion in Middle-Ear Effusions in Patients with Nasopharyngeal Carcinoma", The Laryngoscope, vol. 97, No. 11, 1987, pp. 1295-1298.
Williamson, "Otitis Media with Effusion in Children", BMJ Clin Evid, 2007, vol. 2007, No. 0502, pp. 1-15.
Won, "Low-Coherence Interferometry Otoscope to Quantify Tympanic Membrane Mobility and Middle Ear Pressure", Optics Express, 2018, vol. 9, No. 2, pp. 397-409.
Zhang et al., "Experimental and Modeling Study of Human Tympanic Membrane Motion in the Presence of Middle Ear Liquid", J. Association for Research in Otolaryngology, 2014, 15 pages.
International Search Report and Written Opinion mailed in International Patent Application No. PCT/US2020/026785 (dated Jul. 2, 2020).
Leskinen et al., "Complications of acute otitis media in children in southern Finland", International Journal of Pediatric Otorhinolaryngology, 2004, vol. 68, No. 3, pp. 317-324.
Mandel et al. "Efficacy of Myringotomy with and without Tympanostomy Tubes for Chronic Otitis Media with Effusion", Pediatr Infect Dis J, 1992, vol. 11, No. 4, pp. 270-277.
Marom et al., "Trends in Otitis Media—Related Health Care Use in the United States, 2001-2011", JAMA Pediatrics, 2014, vol. 168, No. 1, pp. 68-75.
Medisave, "Using Otoscopes in Ear Examinations", 2018, <www.medisave.co.uk/using-otoscopes-in-ear-examinations>, 4 pages.
Neto et al., "Risk Factors for Recurrent Acute Otitis Media and Chronic Otitis Media with Effusion in Childhood", Otitis Media: State of the Art Concepts and Treatment, Chapter 4, 2015, pp. 23-32.
Northside Audiology, "Interpreting the Tests—Audiogram and Tympanogram", <northsideaudiology.com.au/interpreting-test-results/>, 2015, 6 pages.
NorthwestENT, YouTube Video, "View of Left Ear Canal and Ear Drum (Tympanic Membrane)", 2009, <https://www.youtube.com/watch?v=krNXVWa8QTg>.
Onerci, "Complications of Otitis Media", Diagnosis in Otorhinolaryngology, 2009, pp. 43-44.
Onusko, "Tympanometry", Am Fam Physician, 2004, vol. 70, No. 9, pp. 1713-1720.
Oyiborhoro et al., "Efficacy Of Acoustic Otoscope In Detecting Middle Ear Effusion In Children"m The Laryngoscope, 1987, vol. 97, No. 4, pp. 495-498.
Parker et al., "Variation in Utilization and Need for Tympanostomy Tubes across England and New England ", The Journal of Pediatrics, 2016, vol. 179, pp. 178-184.
Paul et al. "Teaching the Pediatric Ear Exam and Diagnosis of Acute Otitis Media: a Teaching and Assessment Model In Three Groups", BMC Medical Education, 2017, vol. 17, No. 146, pp. 1-6.
Pelton et al., "Acute Otitis Media in Children: Epidemiology, Microbiology, Clinical Manifestations, and Complications", UpToDate, Inc., 2018, <www.uptodate.com/contents/acute-otitis-media-in-children-epidemiology-microbiology-clinical-manifestations-and-complications?topicRef=5966&source=see_link#H428761755>, 39 pages.
Plasschaert et al., "Trends in Doctor Consultations, Antibiotic Prescription, and Specialist Referrals for Otitis Media in Children: 1995-2003", Yearbook of Pediatrics, 2008, vol. 2008, pp. 102-104.
Preston, "Pneumatic Otoscopy: A Review Of The Literature", Issues in Comprehensive Pediatric Nursing, 1998, vol. 21, No. 2, pp. 117-128.
Qureishi et al., "Update on otitis media-prevention and treatment", Infection and Drug Resistance, 2014, vol. 7, pp. 15-24.
Schwartz, "Pneumatic Otoscopy: An Old Diagnostic Tool Revisited", Healio Infectious Diseases in Children, 2007, <https://www.healio.com/news/pediatrics/20120325/pneumatic-otoscopy-an-old-diagnostic-tool-revisited>, 5 pages.
Staab, "Eardrum Rupture—At What Pressure?", Hearing Health & Technology Matters, 2012, <hearinghealthmatters.org/waynesworld/2012/eardrum-rupture-at-what-pressure/>, 9 pages.
The Hearing Consultancy, "Tympanometry", <thehearingconsultancy.ie/tympanometry/>, 2020, 6 pages.

(56) References Cited

OTHER PUBLICATIONS

Van der Jeught et al., "Real-time structured light-based otoscopy for quantitative measurement of eardrum deformation". Journal of Biomedical Optics, 2017, vol. 22, No. 1, pp. 160008-1-10.

von Unge et al., "Tympanic Membrane Displacement Patterns in Experimental Cholesteatoma", Hearing Research, 1999, vol. 128, No. 1-2, pp. 1-15.

Wallace et al., "Surgical Treatments for Otitis Media With Effusion: A Systematic Review", Pediatrics, 2014, vol. 133, No. 2, pp. 296-311.

European Patent Office Extended European Search Report for application 20784490.3, dated Nov. 10, 2022 (9 pages).

\* cited by examiner

Pneumatic Otoscope

Pediatrician
Primary Care Physician
ENT

Tympanometry

ENT Specialist

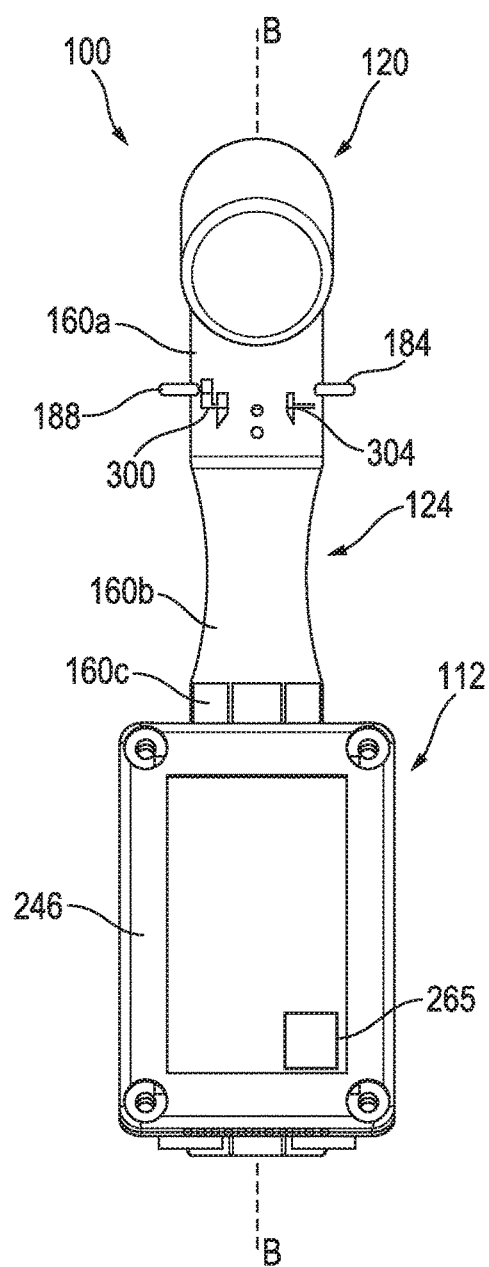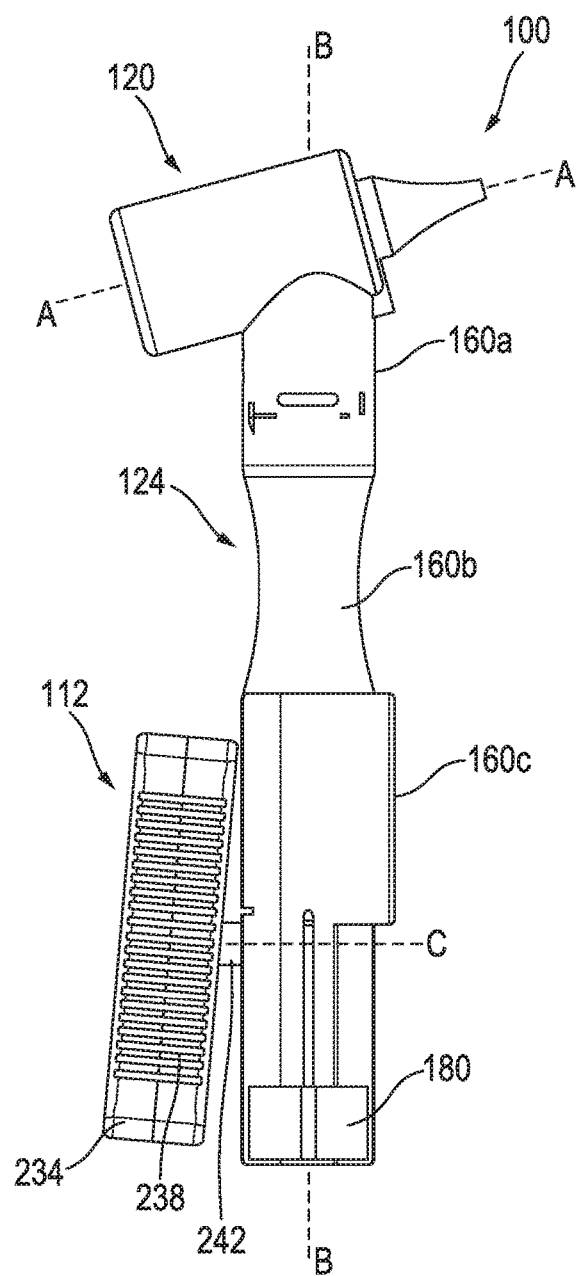
FIG. 3
FIG. 4A

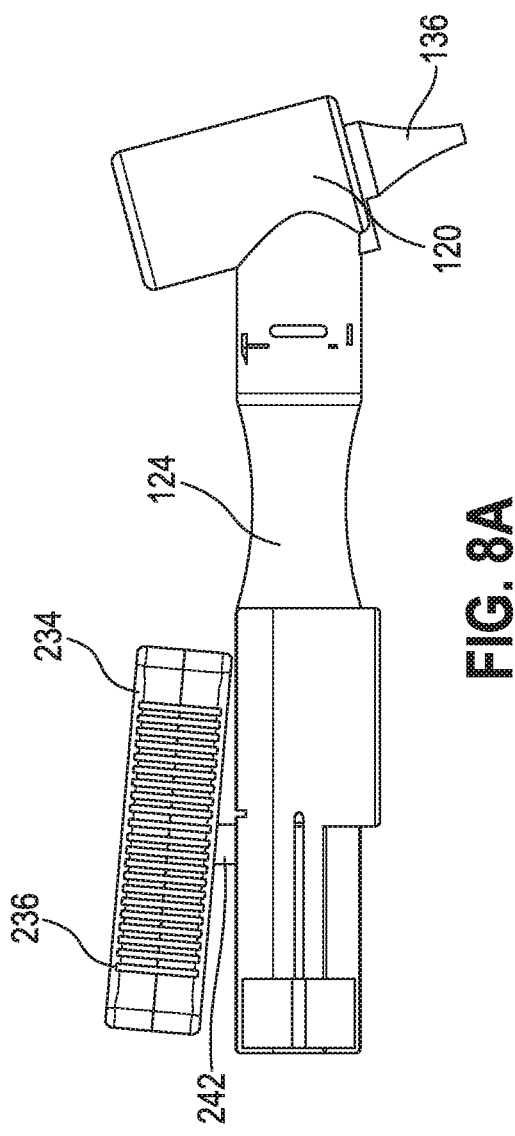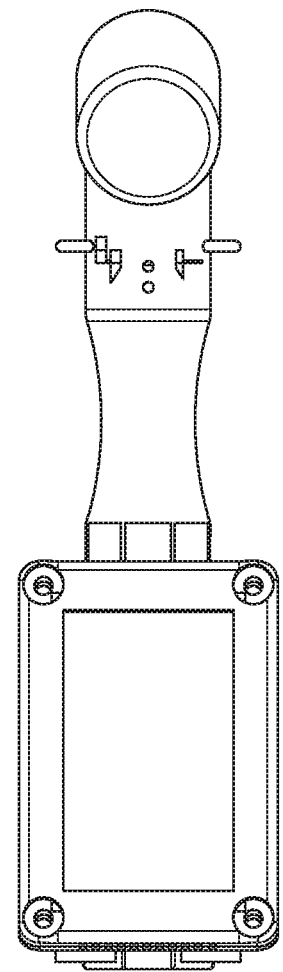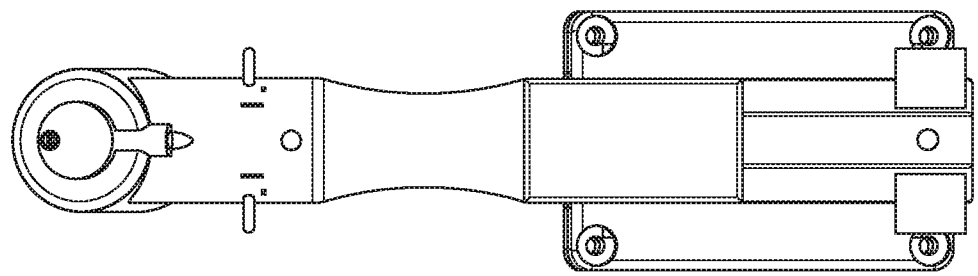

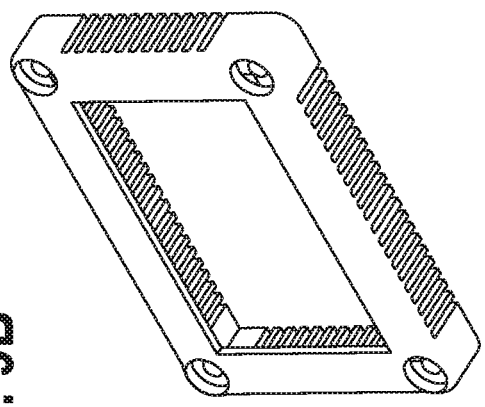
FIG. 9D
FIG. 9B
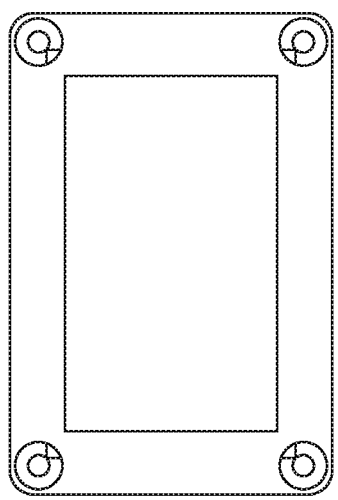
FIG. 9A
FIG. 9C

OTOSCOPE

CROSS-REFERENCE TO RELATED APPLICATION(S)

This application is a U.S. national stage entry of International Patent Application No. PCT/US2020/026785, filed on Apr. 5, 2020, which claims the benefit of U.S. Provisional Patent Application No. 62/829,955, filed on Apr. 5, 2019, the entire contents of each of which are fully incorporated herein by reference.

BACKGROUND

There are two types of devices that are currently used to diagnose ear infections: pneumatic otoscopes and tympanometric instruments. Pediatricians, primary care physicians, and specialists (e.g., ear, nose, and throat (ENT) specialists) use pneumatic otoscopes. As shown in FIG. 1, these devices have a viewing window and bulb attached to them that allows the physician to apply pressure to the tympanic membrane. The physician then looks through the viewing window to observe the movement of the tympanic membrane or lack thereof. Tympanometric instruments (not shown) are only used by ENT specialists and include a probe that is placed in the ear of the patient. As various stimuli are applied to the tympanic membrane, the probe measures the changes in the movement of the tympanic membrane to create a tympanogram, such as the one shown in FIG. 2, which is evaluated by the ENT specialist to determine a diagnosis.

Although the tympanogram provides a quantitative diagnosis for the ENT specialist, they are not the go-to device for such diagnoses. Also, tympanograms are not used by pediatricians and primary care physicians. Moreover, current otoscopes used by pediatricians and physicians do not provide a quantitative method for determining whether or not the tympanic membrane complied in response to a pressure stimulus. These physicians must rely on what they see during an exam that only lasts seconds. Because of this, they are not able to reliably determine whether or not the patient has an ear infection. If they misdiagnose the ear infection, they are sending a healthy patient to an ENT specialist or sending an unhealthy patient home.

SUMMARY

In one construction, an otoscope includes a handle, a housing coupled to the handle and having an inlet, a laser assembly at least partially enclosed within the handle and configured to selectively project, through the inlet, a grid array of dots on a tympanic membrane of a patient, a camera supported by one of the handle or the housing and configured to selectively capture activity of the tympanic membrane, a pressure transducer supported by one of the handle or the housing and configured to selectively apply a stimulus to the tympanic membrane, a display pivotably coupled to the handle, a controller in communication with laser assembly and the display, and a microprocessor in communication with the controller, the camera, and the display. The display is configured to display the tympanic membrane in true color and a two-dimensional interpolated surface plot representing activity of the tympanic membrane in response to the stimulus.

In another construction, an otoscope includes aa handle, a housing coupled to the handle and having an inlet, and a laser assembly at least partially enclosed within the handle and configured to selectively project, through the inlet, a grid array of dots on a tympanic membrane of a patient. The laser assembly includes a laser diode, a diffraction grating, a first lens positioned on a first side of the diffraction grating, and second lens positioned on a second, opposite side of the diffraction grating. The first lens is positioned between the laser diode and the diffraction grating and is a collimating lens. The second lens is a convex lens. The otoscope also includes a camera supported by one of the handle or the housing and configured to selectively capture activity of the tympanic membrane, a pressure transducer supported by one of the handle or the housing and configured to selectively apply a stimulus to the tympanic membrane, a display supported by the handle, a controller in communication with the laser assembly, and the display, and a microprocessor in communication with the controller, the camera, and the display. The microprocessor is configured to measure activity of the tympanic membrane in response to the stimulus applied by the pump based on the changes in distance between each dot of the grid array of dots projected on the tympanic membrane and a central dot of the grid array of dots and configured to construct a two-dimensional plot representing a distance of each dot relative to the center dot of the grid array of dots, and wherein the microprocessor is configured to provide instructions to display the two-dimensional surface plot on the display.

In another construction, an otoscope includes a handle, a housing coupled to the handle and having an inlet, a laser assembly at least partially enclosed within the handle and configured to selectively illuminate, through the inlet, a grid array of dots on a tympanic membrane of a patient, a camera supported within the housing and configured to selectively capture activity of the tympanic membrane, a pressure transducer supported by one of the handle or the housing and configured to selectively apply a stimulus to the tympanic membrane, a display coupled to the handle, a controller in communication with the laser assembly, the camera, and the display, the controller including a memory, and a microprocessor in communication with the controller and the display. The microprocessor is configured to record a video of activity of the tympanic membrane and the display is configured to display real-time video and recorded video.

In another construction, a method of displaying activity of a tympanic membrane of a patient on a display of an otoscope includes illuminating a grid array of dots on the tympanic membrane, applying a stimulus to the tympanic membrane, measuring, in response to the stimulus, changes in distance between each dot of the grid array of dots projected on the tympanic membrane and a center dot of the grid array of dots, constructing a topographical surface plot from the two-dimensional surface plot, and displaying, on the display, the tympanic membrane and the topographical surface plot. The method further includes capturing activity of the tympanic membrane in real-time and displaying, on the display, the real-time activity. The method further includes recording the response of the tympanic membrane to the stimulus.

BRIEF DESCRIPTION OF THE DRAWINGS

FIG. 3 is a rear view of an otoscope according to one construction including an housing, a handle, and a display.

FIG. 4A is a side view of the otoscope of FIG. 3.

FIG. 8A shows another side view of the otoscope of FIG. 3.

FIG. 8B shows a front view of the otoscope of FIG. 3.

FIG. 8C shows a rear view of the otoscope of FIG. 3.

FIG. 9A shows a front view of the display of the otoscope of FIG. 3.

FIG. 9B shows a first side view of the display of the otoscope of FIG. 3.

FIG. 9C shows a perspective view of the display of the otoscope of FIG. 3.

FIG. 9D shows a top view of the display of the otoscope of FIG. 3.

DETAILED DESCRIPTION

Figure 1:
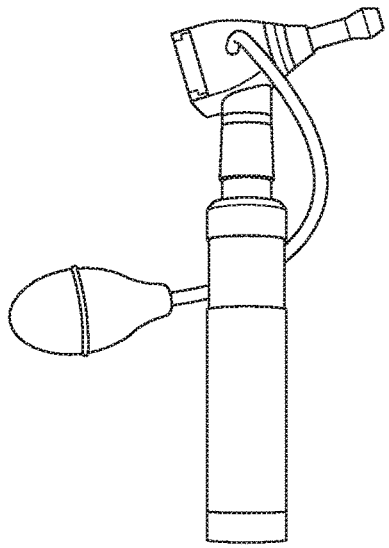
FIG. 1 is a side view of a pneumatic otoscope of the prior art.
Figure 2:
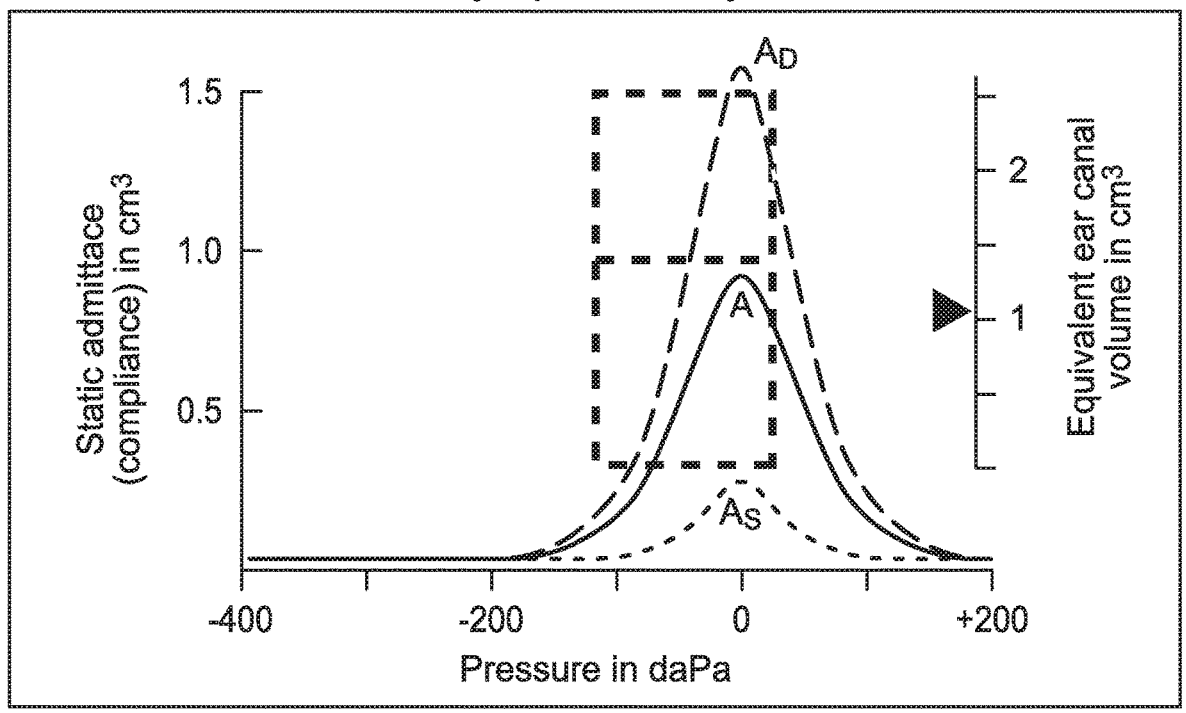
FIG. 2 is an exemplary tympanogram of the prior art.
Figure 4B:
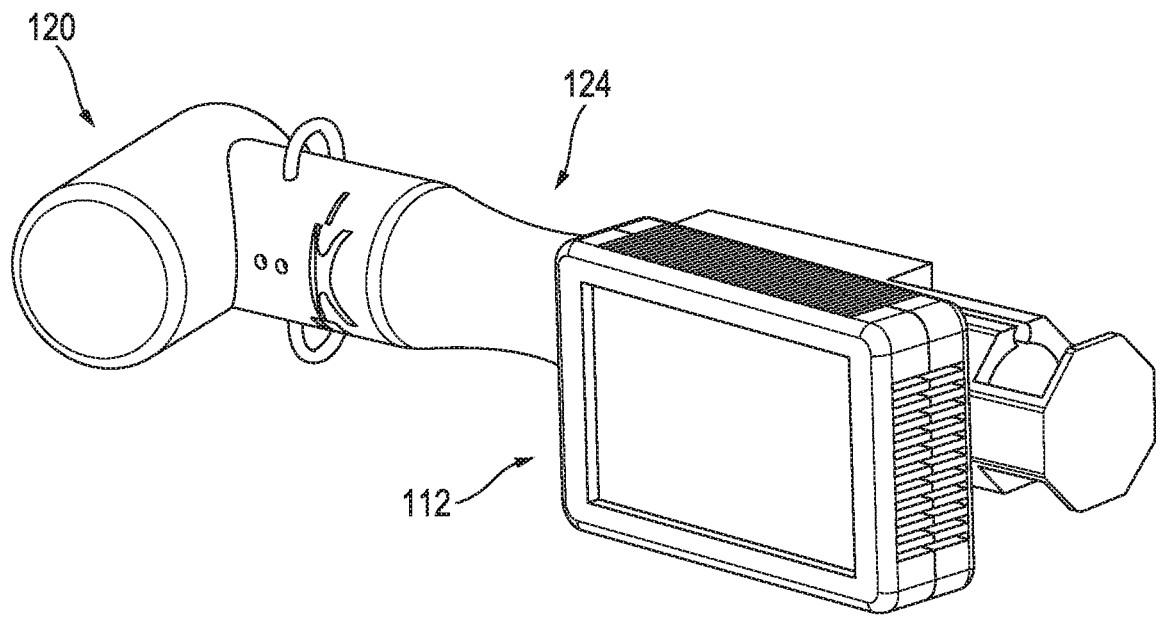
FIG. 4B is a perspective view of the otoscope of FIG. 3.
Figure 4C:
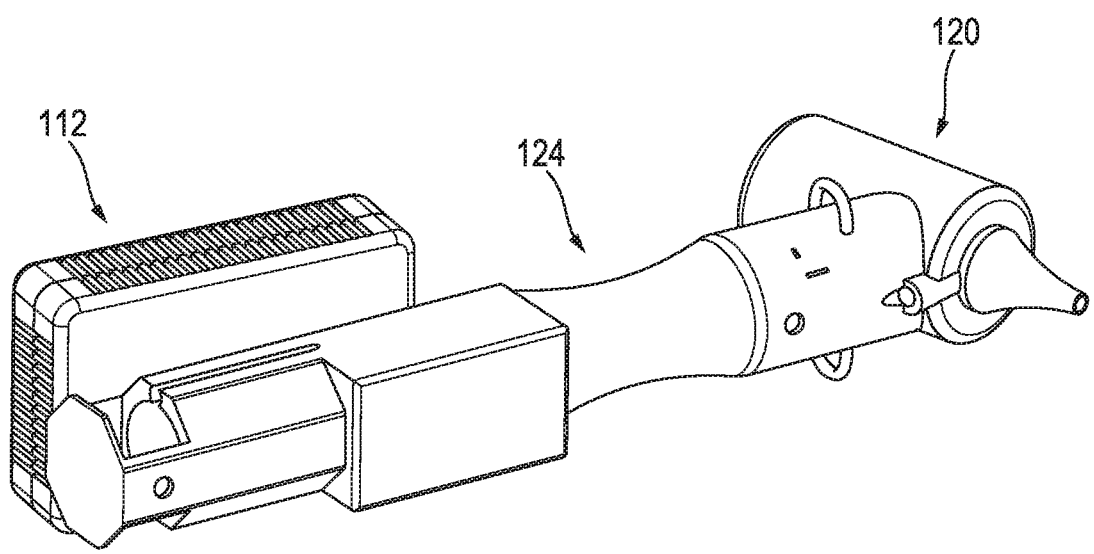
FIG. 4C is another perspective view of the otoscope of FIG. 3.

One or more constructions are described and illustrated in the following description and accompanying drawings. These constructions are not limited to the specific details provided herein and may be modified in various ways. Furthermore, other constructions may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some constructions described herein may include one or more electronic processors configured to perform the described functionality by executing instructions stored in non-transitory, computer-readable medium. Similarly, constructions described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

Use of "including" and "comprising" and variations thereof as used herein is meant to encompass the items listed thereafter and equivalents thereof as well as additional items. Use of "consisting of" and variations thereof as used herein is meant to encompass only the items listed thereafter and equivalents thereof. Unless specified or limited otherwise, the terms "mounted," "connected," "supported," and "coupled" and variations thereof are used broadly to encompass both direct and indirect mountings, connections, supports, and couplings.

As described herein, terms such as "front," "rear," "side," "top," "bottom," "above," "below," "upwardly," "downwardly," "inward," and "outward" are intended to facilitate the description of the lighting device of the application, and are not intended to limit the structure of the application to any particular position or orientation.

FIGS. 3-7 illustrate an otoscope 100 according to a construction. As will be discussed in greater detail below, the otoscope 100 allows visualization of the compliance of the tympanic membrane in response to a pressure stimulus. This change in compliance may also be represented as a topographic map in real-time. Moreover, the patient examination is recorded and may also be viewed after the examination is completed as a looped video on a touchscreen display.

With reference to FIGS. 3-4C and 7, the otoscope 100 includes a housing 120 coupled to a handle 124. The housing 120 includes a longitudinal axis A (shown in FIG. 7) and encloses an optical system 104 within a compartment 128. The housing 120 includes a mount 132 configured to removably receive and secure a speculum 136. Standard specula 136 have a cone-shaped body with a coupling end 144, which is coupleable to the mount 132, and an outlet 148. The outlet 148 includes a diameter that is smaller than a diameter of the inlet 144. The mount 132 includes an aperture 152 (FIG. 7) extending therethrough. The aperture 152 is in communication with the compartment 128 of the housing 120, aligns with the longitudinal axis A of the housing 120, and is configured to align with the outlet 148 of a standard speculum 136.

Further, with respect to FIGS. 4A-C and 7, the handle 124 has a body 160 that defines a longitudinal axis B. The handle 124 includes a compartment 162 that supports a camera 164, a light (e.g., a halogen lamp) 168, a controller 172 (e.g., a microcontroller, such as a nano Arduino board), a power source 176 (e.g., one or more replaceable 3.7 V batteries or one or more rechargeable batteries having any suitable voltage), a stimulus system 108, and a microprocessor 250 (e.g., a Raspberry pi 3 B+, an application-specific integrated circuit (ASIC), another suitable electronic device). In the embodiment of FIGS. 1-13, the stimulus system 108 includes a pressure transducer 180, such as a pump.

In one construction, the body 160 of the housing 124 is formed by injection molding. Also, the body 160 is coupled together by a snap fit configuration for easy and secure assembly. Other methods of forming the body 160 of the housing 124 are additionally contemplated, however. As shown in FIGS. 3 and 4A-C, the body includes a first section 160a that is coupled to the housing 120, a second section 160b that extends from the first section 160a and varies in diameter (e.g., is substantially hour-glass shaped), and a third section 160c that extends from the second section 160b and is distal from the housing 120. In the illustrated construction, the pump 180 is positioned in the third section 160c (a distal end) of the handle 124. The pump 180 may be a peristaltic pump, but in other or alternative constructions, any suitable type of pump may be utilized.

The handle 124 also includes a first projection 184 and a second projection 188 extending from the first section 160a of the handle 124. The first and second projections 184, 188 are positioned near the housing 120 and are configured to support one of the index finger and thumb of the healthcare provider or healthcare provider while the otoscope 100 is in use. The first and second projections 184, 188 are substantially arcuate and project from opposite sides of the handle 124.

The handle 124 is symmetrical about the longitudinal axis B when viewed from the rear (FIG. 3) such that the otoscope 100 is useable by both right-handed and left-handed healthcare providers. Additionally, the handle 124 is configured to be held comfortably by the healthcare provider. That is, the handle 124 has a length of approximately 30 cm, a width of approximately 8 cm, and a depth of approximately 8.5 cm. The dimensions of the handle 124 may have any suitable dimensions, however. Moreover, the entire otoscope is lightweight, and may weigh approximately 400 grams to approximately 600 grams. In one construction, the otoscope 100 is approximately 500 grams. The weight of the otoscope 100 may have any suitable dimensions, however.

The otoscope 100 is formed from a material that is impact resistant, easily manufacturable, and corrosion resistant. An exemplary material includes acrylonitrile butadiene styrene (ABS), although any suitable material is within the scope of this disclosure. Moreover, the otoscope 100 may also include an overmold formed of a material that is abrasion resistant and chemical resistant, such as a thermoplastic polyurethane elastomer (e.g., Versaflex™ OM 6258, owned by PolyOne™) or the like. The first and second projections 184, 188 are preferably constructed from neoprene rubber or other suitable material.

Figure 5:
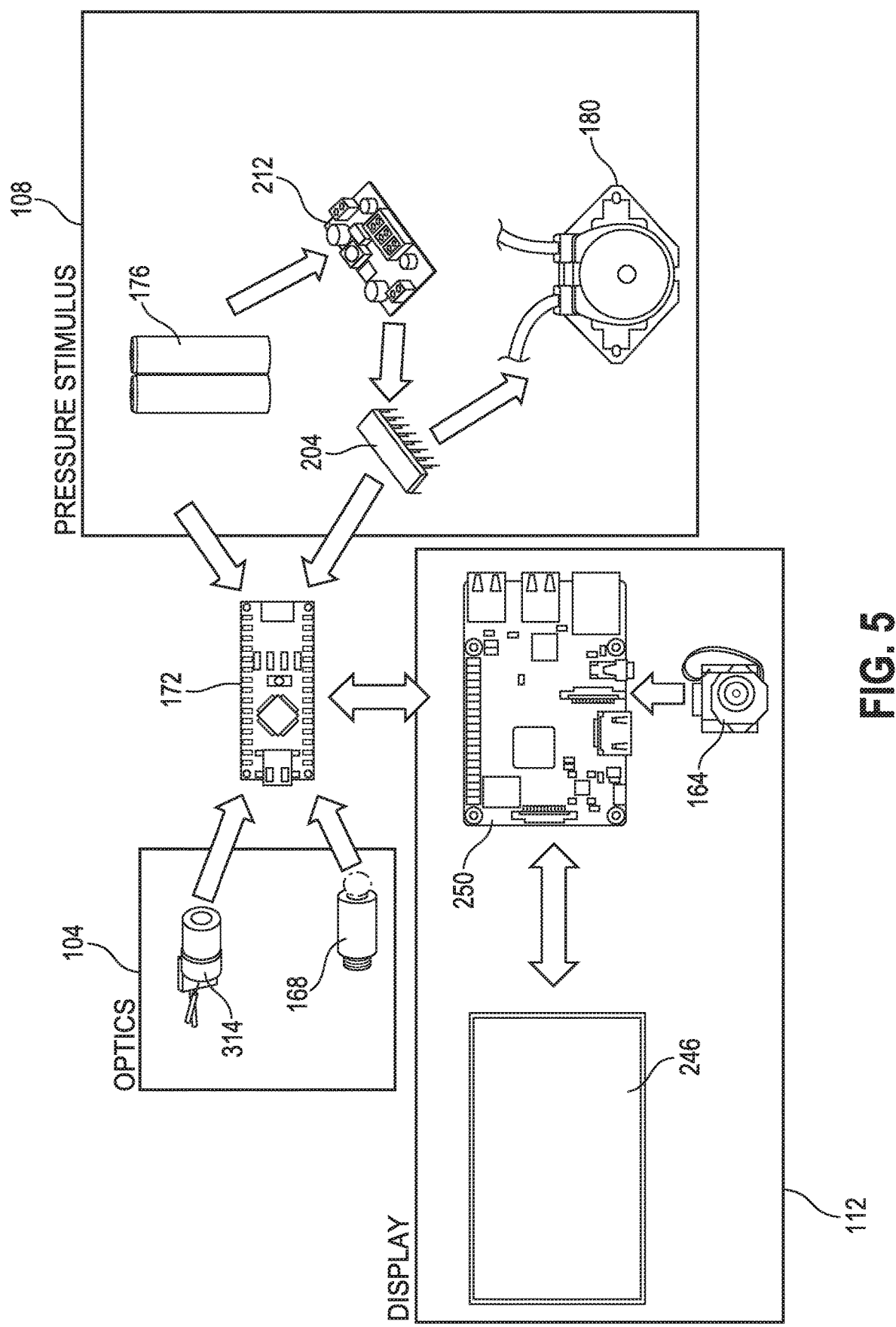
FIG. 5 is a schematic of the functionality of the otoscope of FIG. 3.

With reference to FIG. 5, the controller 172 and is in communication with the microprocessor 250. The controller 172 is in communication with and powers the light 168 and the laser assembly 310, both of which are discussed in greater detail below. The microprocessor 250 includes a computer-readable memory (e.g., storage), a motor driver, a graphics card, a voltage regulator, and a complementary metal-oxide-semiconductor (CMOS) circuit having a CMOS sensor. The microprocessor 250 may also include Wi-Fi, Bluetooth®, cloud processing, a wireless remote control, and enables communication of data to a smartphone, tablet, or computer. These features enable troubleshooting of the otoscope 100 and aggregation of the data at a distance. The microprocessor 250 may include a battery charging circuit, a boost or step-up converter, and a gyroscopic sensor or accelerometer. In one construction, the microprocessor 250 includes memory 200 having a storage capacity of 21.97 GB, and the graphics card 208 includes memory having a storage capacity of 64 GB. The microprocessor 250 is configured to retrieve data from the memory and execute, among other things, software related to the processes and methods described herein. The memory includes a non-transitory, computer-readable storage medium. The voltage regulator is connected to the batteries 176. The battery charging circuit regulates the backward voltage and/or current put into a battery during charging to ensure the batteries are not damaged. This circuit measures the battery charge level. The boost or step-up converter efficiently regulates the voltage from the batteries and increase the voltage to power higher voltage devices such as the computing unit. Additionally, a pressure sensor, which is in communication with the microprocessor 250 and measures the pressure stimulus applied to the tympanic membrane over time, is positioned in either the handle 124 or in the housing 120.

With respect to FIGS. 3-6, the otoscope 100 includes a display 112 being in communication with the microprocessor 250 and having a screen assembly 230 that is movably (e.g., pivotably) coupled to the handle 124. In particular, the screen assembly 230 is coupled to the third section 160c of the handle 124. The display 112 is in communication with the components within the handle 124. As shown in at least FIGS. 3-9H, the screen assembly 230 includes a housing 234 that has vents 238 on each side thereof for dissipating heat from the housing 234, a projection 242 extending therefrom, and a screen 246 positioned within the housing 234. The screen 246 is capacitive and is constructed from a glass substrate that has a conductive coating (such as an indium tin oxide (ITO) coating) that is operable with surgical gloves. The gyroscopic sensor or accelerometer determines screen 246 orientation and stabilizes video. The gyroscopic sensor or accelerometer may be stored anywhere in the otoscope 100 to determine the device orientation over time and compare it with the video during processing and to flip the display (90° or 180°) if the healthcare provider inverts the device.

The projection 242 is coupled to the handle 124 and defines a projection axis C (FIG. 4A) that is perpendicular to the longitudinal axis B of the handle 124. The display housing 234 is pivotable about the projection axis C relative to the handle 124 to change the viewing angle of the screen 246. With respect to FIGS. 10 and 11, the screen 246 displays a graphical user interface 254 (GUI) that is a touch screen and may be configured to display one or more of the following: a battery life display 258, a true-color display 260 of the tympanic membrane, an overlay display 262, a topographical display 264, a pressure of the ear canal, a pressure vs. time display 265 (FIG. 3), a color bar 266, file name 270, a save actuator 274, a view cycle actuator 278, and actuators 282a, 282b, 282c, 282d corresponding, respectively, to fast forward, reverse, pause, and play. The "fast forward" actuator may instead be a video speed actuator that allows the healthcare provider to pick a speed of the video, such as 0.25×, 0.5×, 0.75×, 1×, 1.25×, 1.5×, 1.75×, 2×, etc.

The microprocessor 250 of the otoscope 100 is configured to capture color video at a frequency of 22.5 Hz plus/minus 3 Hz (e.g., input frequency) and interlace it to 45 Hz plus/minus 6 Hz display format (e.g., output frequency). In one construction, the spatial resolution displayed is limited to the touch screen's 800×480 pixels, but the CMOS sensor can switch its resolution between capturing 8-bit true-color display of 640×480 pixels at 90 Hz and 3-bit laser dot grid spatial measurement of 1920×1080 pixels at 30 Hz. The display microprocessor 250 can process and output to the screen 246 the 8-bit true-color of the ear canal to the touch screen at 45 fps with a common baud rate of 9600 bps. In one construction, the average processing speed of the otoscope 100 is a minimum of 195.26 Mbps and the maximum processing speed is 221.18 Mbps. It is noted that as components improve through technological advances, processing speeds will increase and the otoscope described herein is not limited to the minimum or maximum processing speeds mentioned. The color bar ranges from −1 mm to 1 mm with max and min displacement labels. While performing the exam, the screen 246 includes a border that has a first color (e.g., green) that denotes correct placement in the ear (14 mm plus/minus 0.5 mm) between specula and tympanic membrane, a second color (e.g., orange) for nearly correct placement in the ear (14 mm to tympanic membrane plus/minus 1 mm), and a third color (e.g., red) for incorrect or dangerous placement. In the illustrated construction, the screen 246 is approximately 4 inches wide, however additional suitable sizes may be implemented.

The otoscope 100 also includes one or more physical actuators (e.g., buttons) coupled to the handle 124. In the illustrated construction, the otoscope 100 includes a stimulus actuator 300 and a start/stop record actuator 304.

Figure 7:
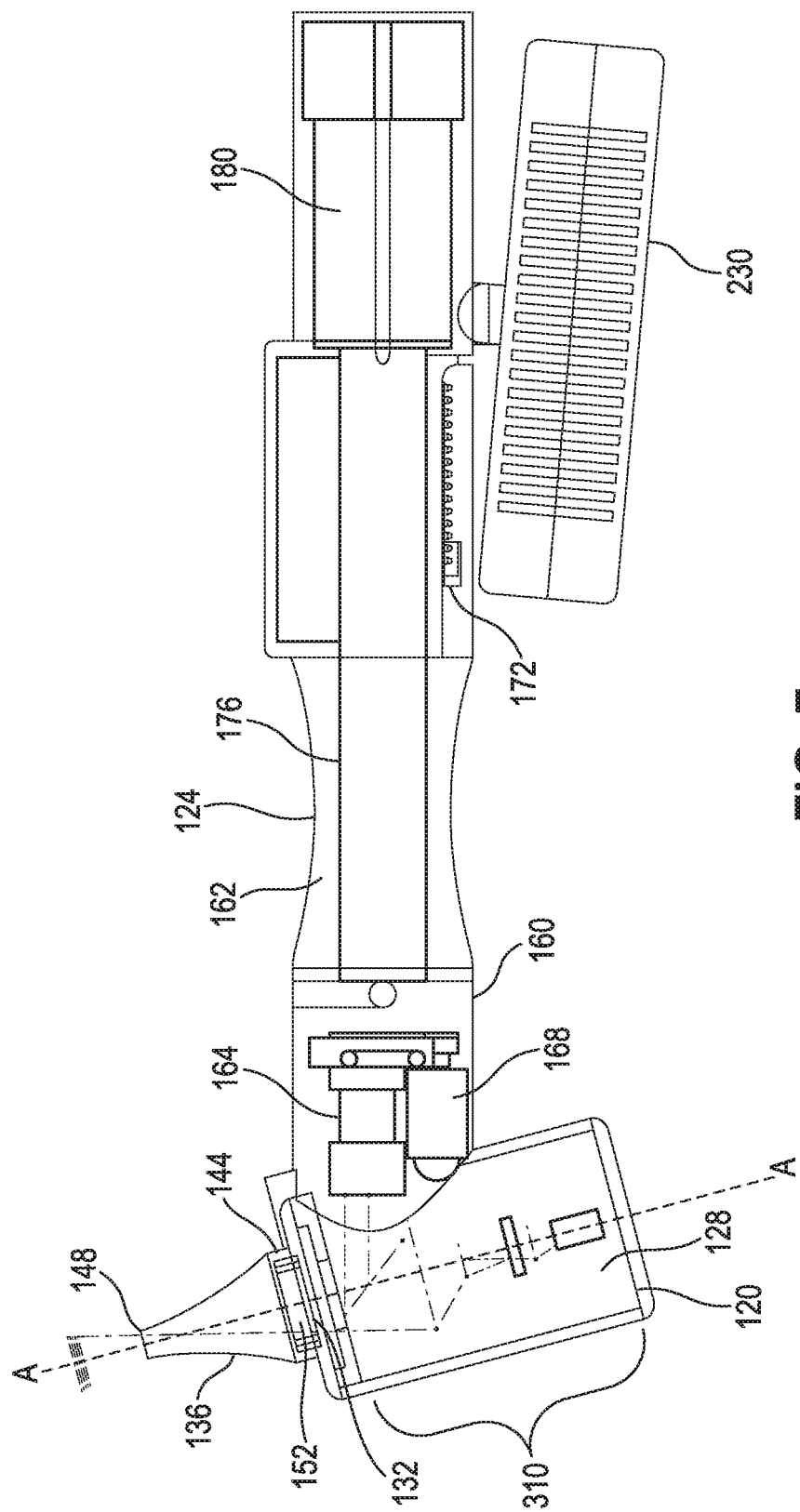
FIG. 7 is cross-section view of the otoscope of FIG. 3 taken along a longitudinal axis of the handle.
Figure 8E:
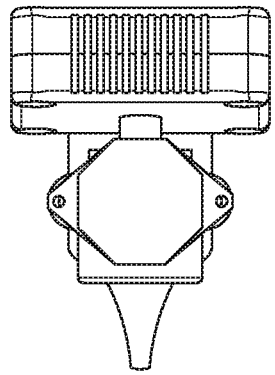
FIG. 8E shows a bottom view of the otoscope of FIG. 3.
Figure 8D:
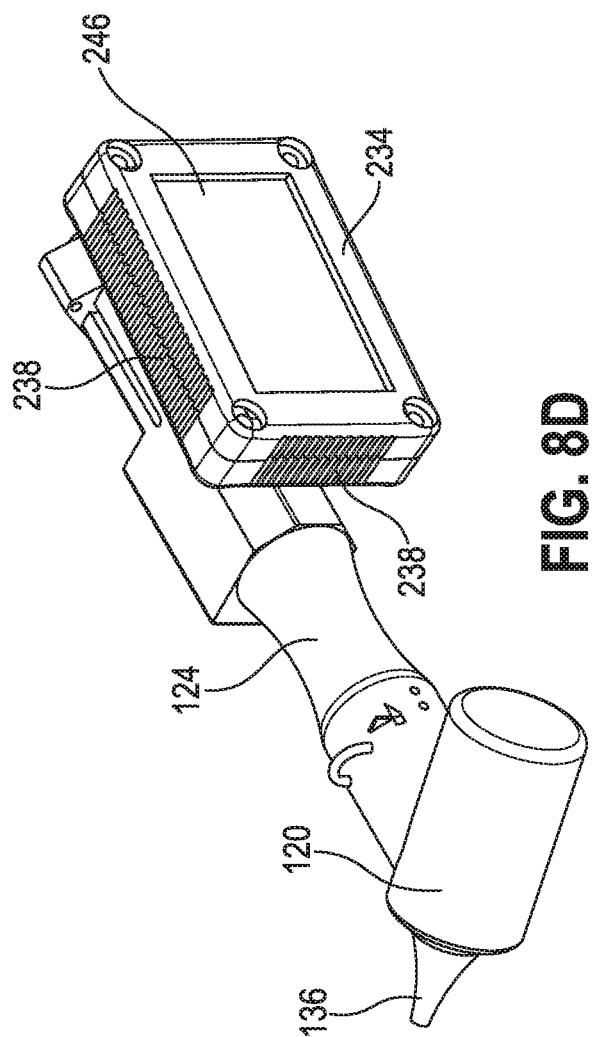
FIG. 8D shows a perspective view of the otoscope of FIG. 3.
Figure 8G:
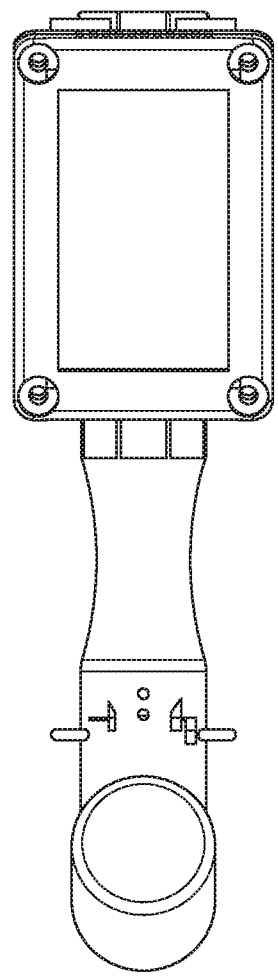
FIG. 8G shows another rear view of the otoscope of FIG. 3.
Figure 8F:
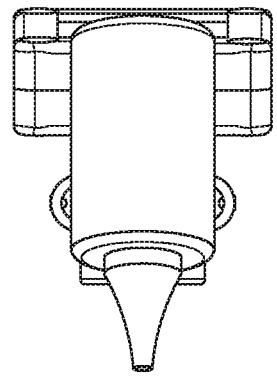
FIG. 8F shows a top view of the otoscope of FIG. 3.
Figure 9H:
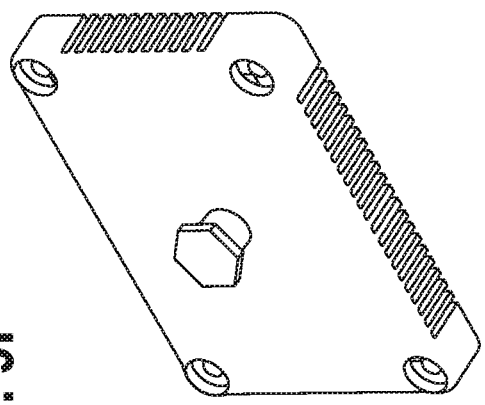
FIG. 9H show another perspective view of the display of the otoscope of FIG. 3.
Figure 9F:
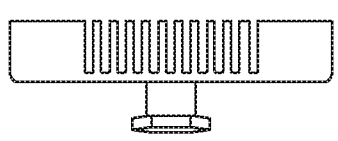
FIG. 9F shows another side view of the display of the otoscope of FIG. 3.
Figure 9E:
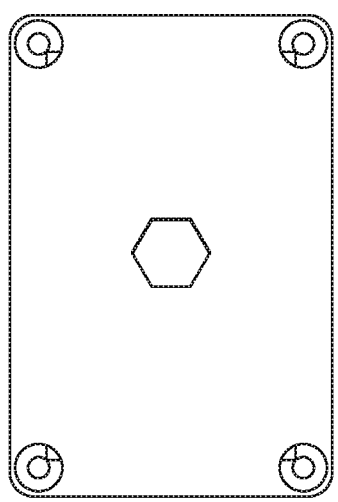
FIG. 9E shows a rear view of the display of the otoscope of FIG. 3.
Figure 9G:
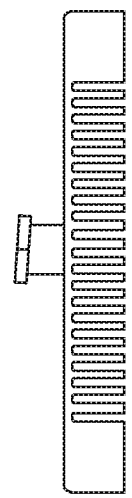
FIG. 9G shows another top view of the otoscope of FIG. 3.
Figure 10:
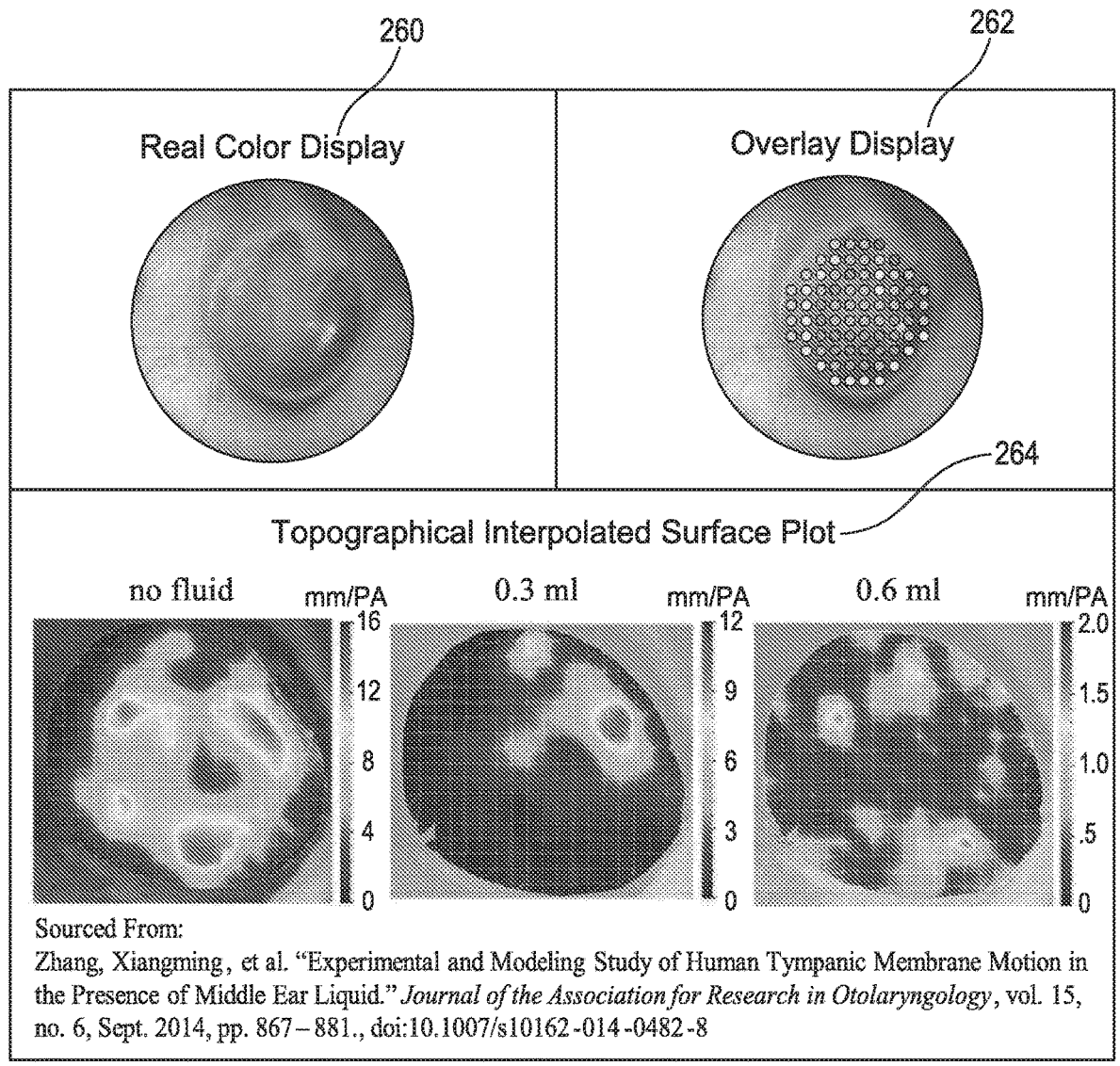
FIG. 10 show exemplary displays that are viewable by a healthcare provider on a graphical user interface of the otoscope of FIG. 3.
Figure 11:
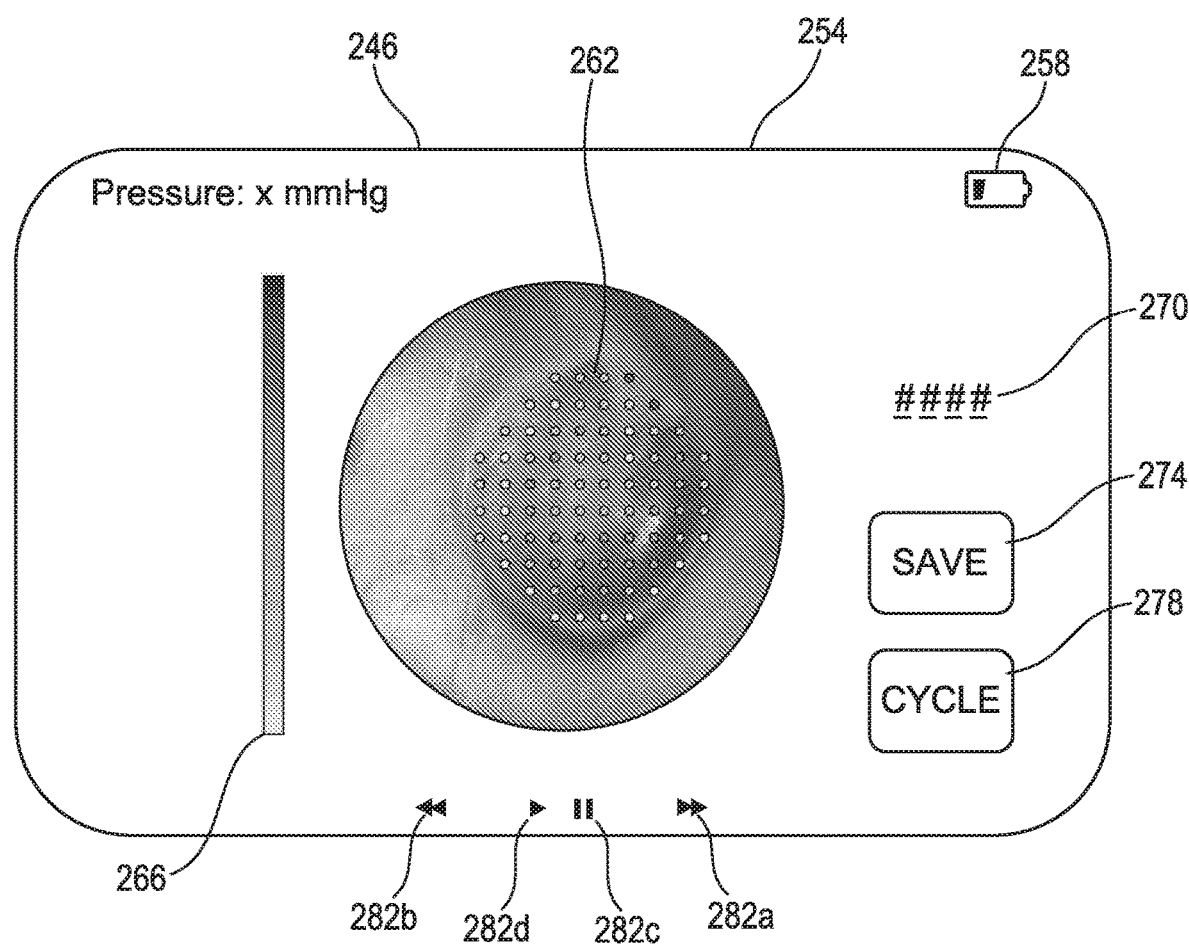
FIG. 11 is another exemplary display that are viewable by a healthcare provider on a graphical healthcare provider interface of the otoscope of FIG. 3.

As shown in FIG. 7, the compartment 128 of the housing 120 is in communication with the compartment 162 of the handle 124. The longitudinal axis A of the housing 120 is oriented at an obtuse angle (e.g., greater than 90-degree angle, FIG. 4) relative to the longitudinal axis B of the handle 124.

Figure 6:
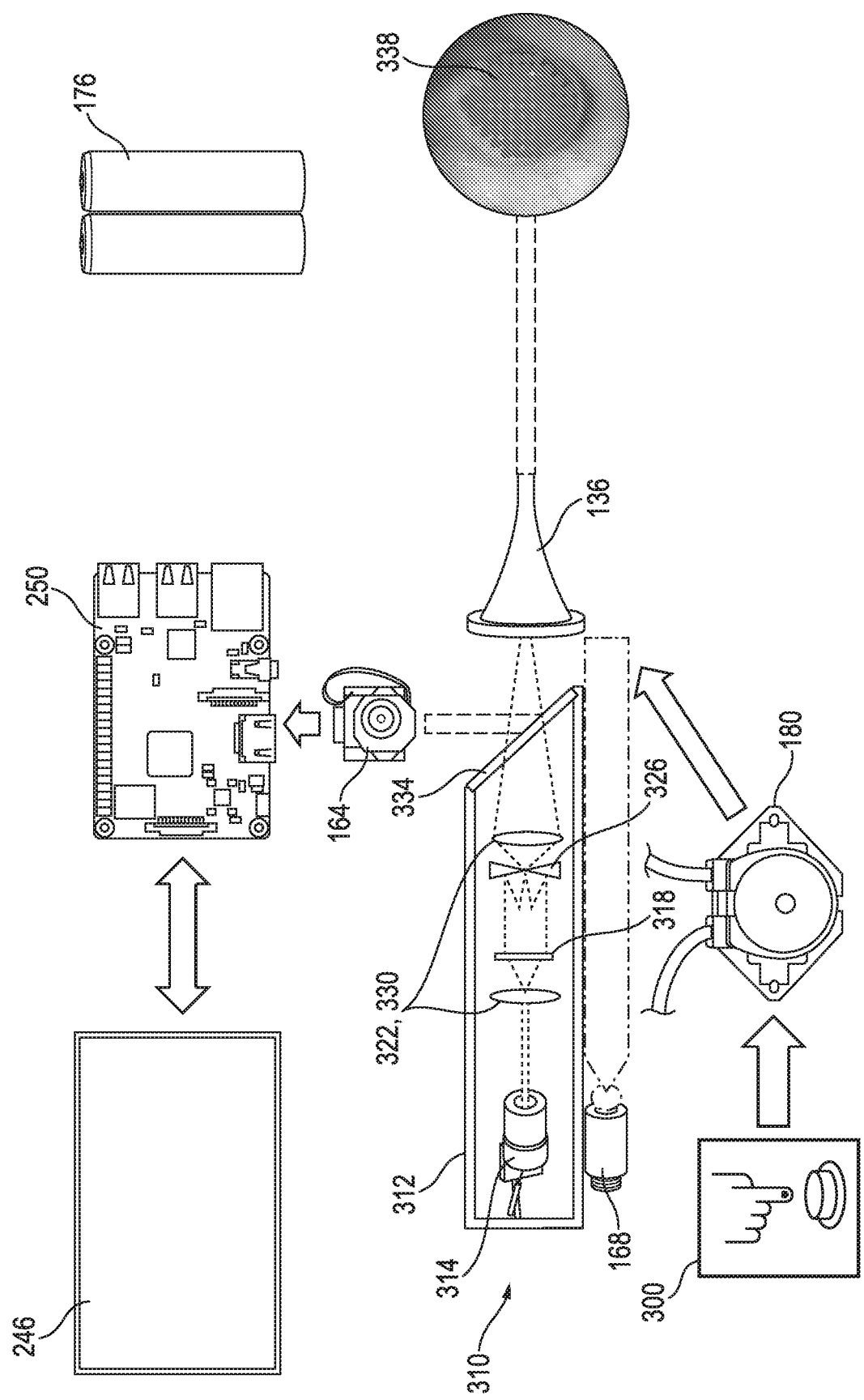
FIG. 6 is another schematic of the functionality of the otoscope of FIG. 3.

Further, with respect to FIGS. 6 and 7, the optical components that are enclosed within the housing 120 include a laser assembly 310. The laser assembly 310 is enclosed within a sub-housing 312 within the housing 120 and includes a laser diode 314, a diffraction grating (DOE) 318, a plurality of lenses 322, 326, 330, and a mirror 334. The laser diode 314, the diffraction grating 318, and the plurality of lenses 322, 326, 330 are aligned along the longitudinal axis A of the housing 120. In particular, the laser diode 314 is positioned adjacent a first convex lens 322, which is positioned adjacent to the diffraction grating 318. A concave lens 326 is positioned adjacent the diffraction grating 318, and a second convex lens 330 is positioned adjacent the concave lens 326 and the mirror 334 in the housing 120. When the light from the laser diode 314 passes through the diffraction grating 318, it is transformed from a single ray into a grid array of dots 338. The grid array of dots 338 is expanded with the concave lens 326 (e.g., diverging lens) and then focused through the aperture 152 in the housing 120 and the outlet 148 of the speculum 136 with the second convex lens 330 (e.g., converging lens). In other or additional constructions, other optical components besides a laser assembly are contemplated.

The light 168 is positioned within the handle 124 and adjacent the sub-housing 312. The light 168 is configured to illuminate the ear canal and tympanic membrane but not to interfere with the laser assembly 310. The light 168 is configured to provide a stable output for a minimum of 30 seconds (for example) to provide consistent illumination to the ear canal. In other or additional constructions, other types of lights besides a halogen lamp are contemplated and the light 168 may be illuminated for less than or greater than 30 seconds.

The microprocessor 250 stores information and executable functions associated with the otoscope 100. That is, the microprocessor 250 communicates with the optical system 104, the stimulus system 108, and the display 112. As shown in FIG. 5, the optical system 104 includes the light 168 and the laser assembly 310. The stimulus assembly 108 includes the power source 176, the pump 180, the motor driver 204, and the voltage regulator 212. The display 112 includes the camera 164 and the screen 246.

Further, with respect to FIG. 5, upon actuation of the stimulus actuator 300, the microprocessor 250 is configured to illuminate the laser diode 314 and light 168 by turning both on, and also is configured to start the motor driver 204 and voltage regulator 212 to cause the pump 180 to apply a stimulus (e.g., pressure) to the tympanic membrane. While the stimulus actuator 300 is actuated, the activity of the tympanic membrane is also captured by the camera 164 and displayed in real-time on the screen 246. Additionally, upon actuation of the start/stop record actuator 304, the controller 172 is configured to cause the microprocessor 250 to record the activity of the tympanic membrane in response to the stimulus from the pump 180. Accordingly, activity of the tympanic membrane that is captured by the camera 164 can be stored by the controller 172 and later exported or transferred (via USB, for example) such that the healthcare provider can re-watch and review the activity of the tympanic membrane later.

Figure 12:
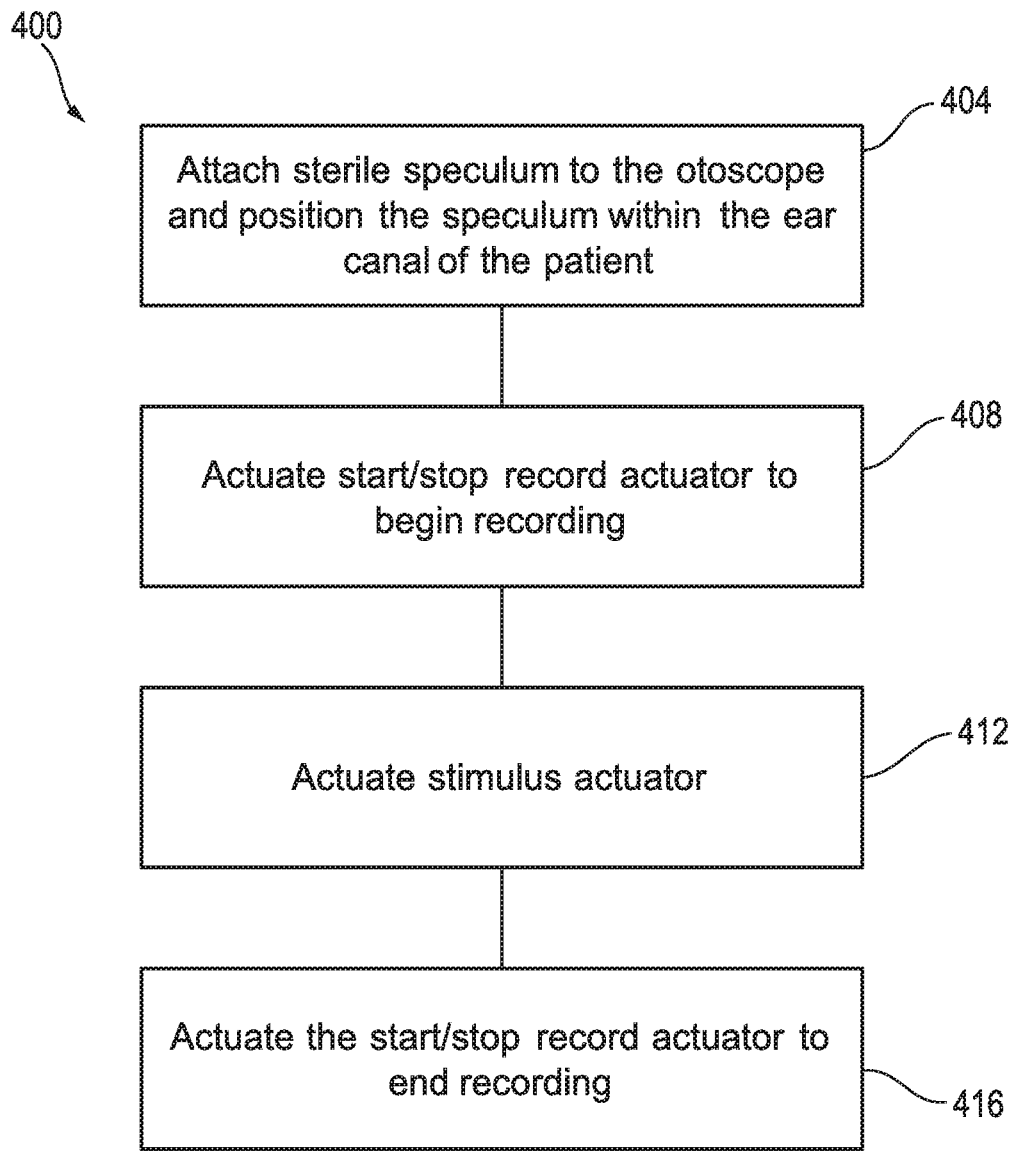
FIG. 12 shows a method of use of the otoscope of FIG. 3.
Figure 13:
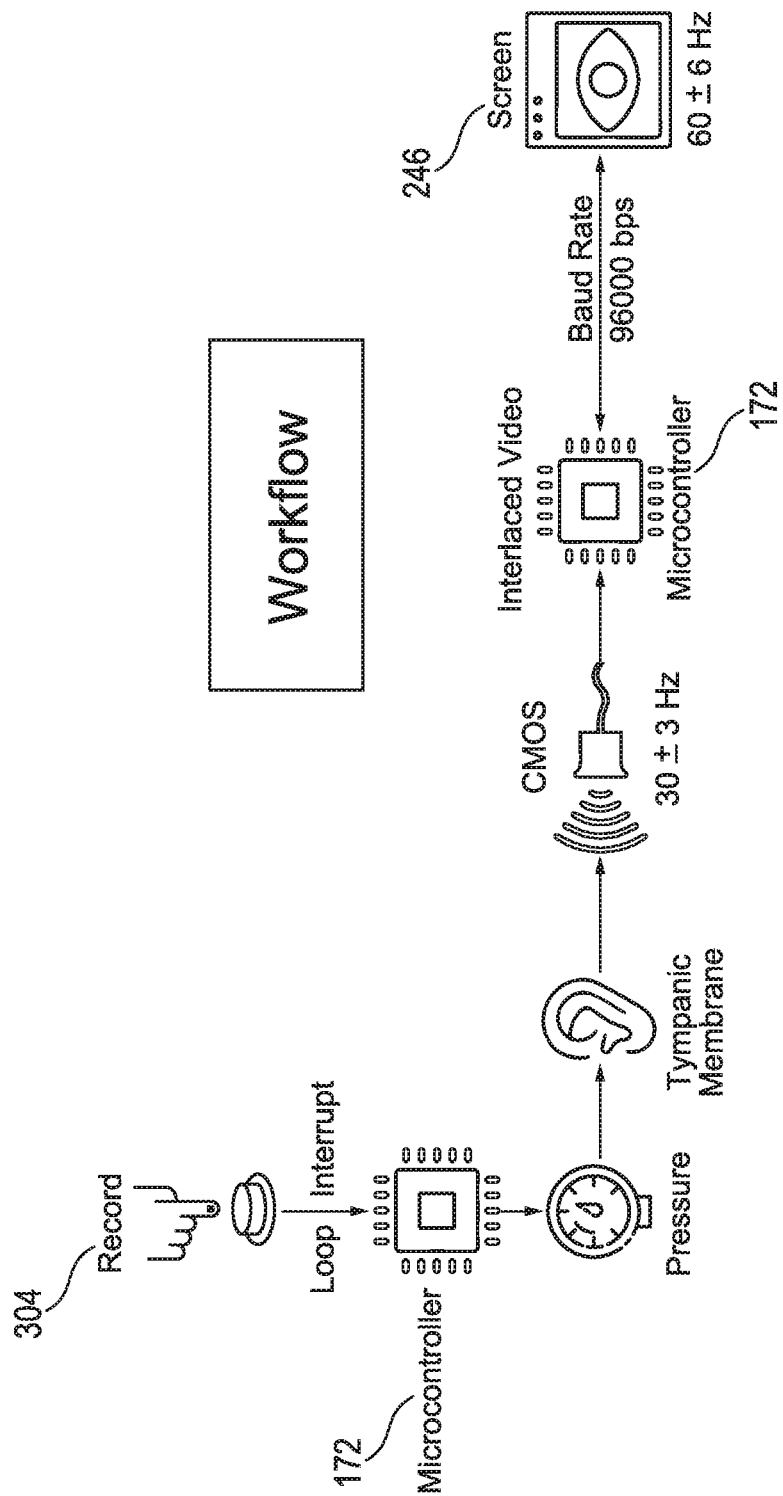
FIG. 13 is a workflow diagram for the display of the FIG. 3.

The flow chart in FIG. 12 illustrates a method 400 of use of the otoscope 100. At step 404, the healthcare provider attaches a sterile speculum 136 to the housing 120 of the otoscope 100, and positions the speculum 136 within the ear canal of the patient. Then, actuation of the start/stop record actuator 304 at step 408 causes the microprocessor 250 to record. As shown in FIG. 13, the first actuation of the start/stop actuator 304 will trigger interrupt protocols so that the microprocessor's 350 current action is halted before the end of its loop. This allows quick response times from the internal control unit 172.

At step 412, the healthcare provider actuates the stimulus actuator 300 such that the microprocessor 250 activates the pump 180, the laser assembly 310, and the light 168. The stimulus actuator 300 may be actuated one or more times by the healthcare provider. Actuation of the stimulus actuator 300 causes the laser assembly 310 to display the grid array of dots 338 on the tympanic membrane of the patient, the light 168 to illuminate the tympanic membrane for a clearer view of the tympanic membrane, and the pump 180, operated through the motor driver 204, to cause positive and negative volume displacement/pressure stimulus (e.g., pressure ranging from 55 mmHg and −55 mmHg) on the tympanic membrane. Additionally, the camera 164 is configured to capture the activity of the tympanic membrane on the screen in real time, while the stimulus button 300 is actuated. That is, the otoscope 100, and specifically the microprocessor 250, is configured to measure the compliance of the tympanic membrane based on the changes in distance between individual dots of the grid array of dots 338 projected on the tympanic membrane. That is, the angle between the dots in the grid array 338 is constant, so a trigonometric algorithm is used to determine the distance from each dot to a focal point based on a distance of a dot to a central dot. The otoscope 100, and specifically the microprocessor 250, is configured to measure a maximal displacement of the tympanic membrane of 100 μm to 1 mm. The activity of the tympanic membrane is viewable by the healthcare provider as a true-color display 260, topographical display 264, and overlay display 262. The true-color display 260 shows no topographical information and illustrates the truest color of the ear canal possible by 8-bit color. The topographical display 264 shows an interpolated two-dimensional ("2D") surface plot that has one or more colors, each of which corresponds to a distance of each of the dots relative to the camera 164 and the laser diode 314. In one construction, the topographical display 264 shows an interpolated two-dimensional ("2D") surface plot that has colors that correspond to the intensity of infrared (IR) dots. The intensity of the IR dots projected onto the tympanic membrane corresponds to the distance of each dot to the center dot. In another construction, the distance information is collected based on the time it takes the light to hit the object and bounce back to the camera from each projected laser dot. This is known as time of flight or TOF. In another construction the distance information is collected based on the wavelength shift of the light from each projected laser dot. This is known as LIDAR. The respective distances are correlated to relative pressure (e.g., in mm/Pa) of the respective area or point on the tympanic membrane. In either construction, as an example, the color blue (and variations thereof) may represent 0 mm/Pa to 5 mm/pa, the color green (and variations thereof) may represent 5 mm/pa to 9 mm/Pa, the color yellow (and variations thereof) may represent 9 mm/Pa to 10 mm/Pa, the color orange (and variations thereof) may represent 10 mm/Pa to 12 mm/Pa, and the color red (and variations thereof) may represent above 12 mm/Pa. The overlay display 262 is a combination of both the true-color and topographical information, where the topographical information is not interpolated (e.g., two-dimensional non-interpolated surface plot) and is instead represented with the grid array of dots, each having a color corresponding to the respective distance (e.g., relative pressure) as discussed above with respect to the topographical display 264. The overlay display 262 is associated with the color bar 266 indicating level display, which relates displacement of the tympanic membrane relative to measured dot displacement.

Actuation of the start/stop record actuator 304 at step 416 will stop the microprocessor 250 from recording. The second actuation of the start/stop actuator 304, which ends the video capture, will initiate the processing of the entire duration of the video capture and will quickly lead to the looped video display of the diagnostic examination on the screen 246 of the otoscope 100.

As discussed above, the microprocessor 250 includes 195.26 Mbps of storage, which allows a healthcare provider to record the examination for a maximum of one minute per patient (e.g., there is enough storage for 1.46 GB per patient). All looped video displays will show a graphic 265 that is a plot that illustrates the relationship between maximal tympanic membrane deflection and the applied pressure. This graphic is positioned in the corner of the screen 246 so that it does not interfere with the visualization of the tympanic membrane. The healthcare provider can use actuators 274, 278 of the screen 246 to save videos to internal storage or delete them. Deleting the video will instantaneously clear the screen 246 and display the manufacturer's logo. The healthcare provider may also toggle between the real-time video feature and the record feature. In particular, when recording, the healthcare provider can press the start/stop record actuator 304 (after either saving or deleting the recording) to return to the real-time video feature. In the illustrated construction, this procedure can be repeated as many times as the clinician desires, but only one video will ever be stored on the device at a time. In other or additional constructions, multiple videos may be stored to the device, however.

Figure 14:
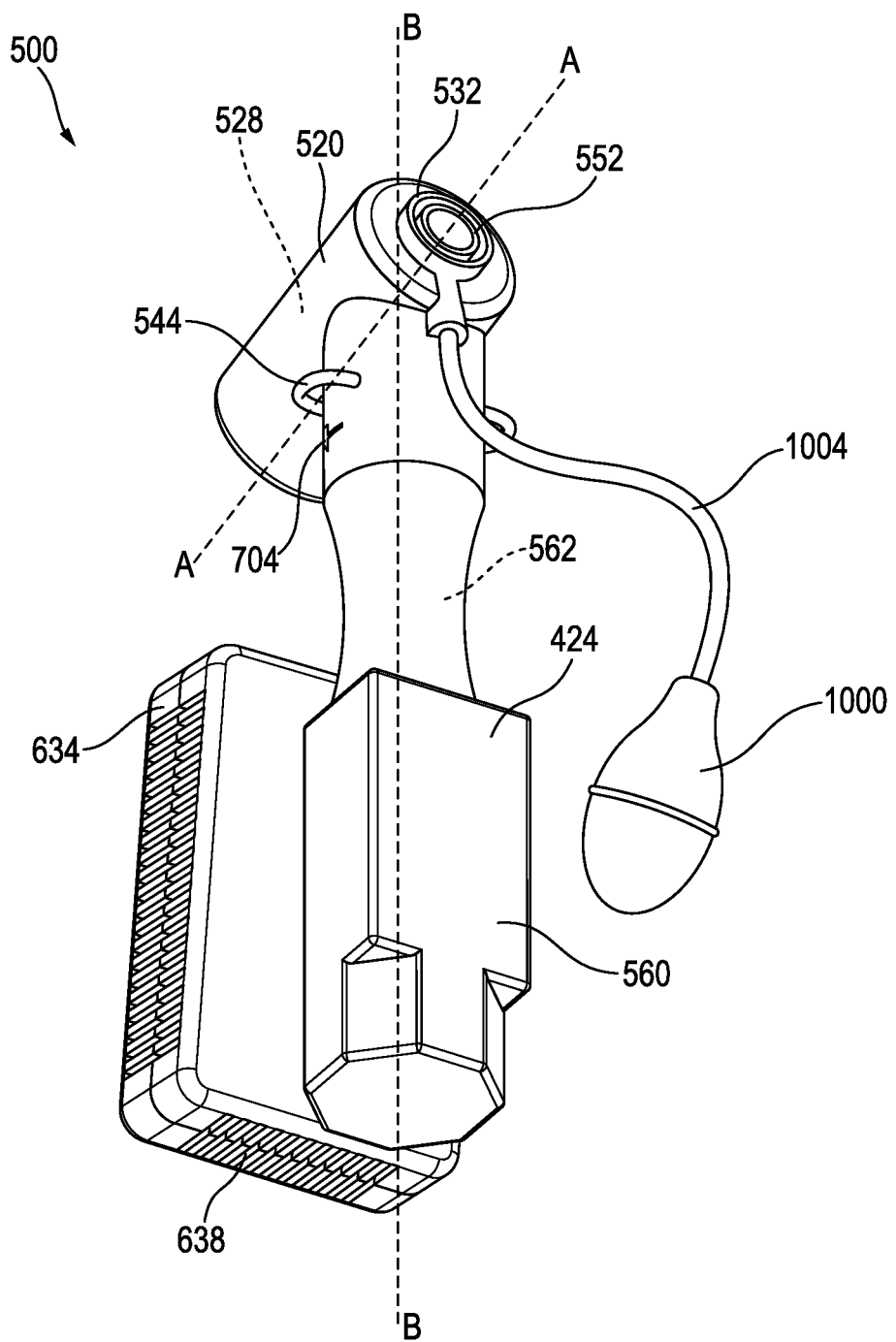
FIG. 14 illustrates a perspective view of another embodiment of an otoscope.
Figure 15:
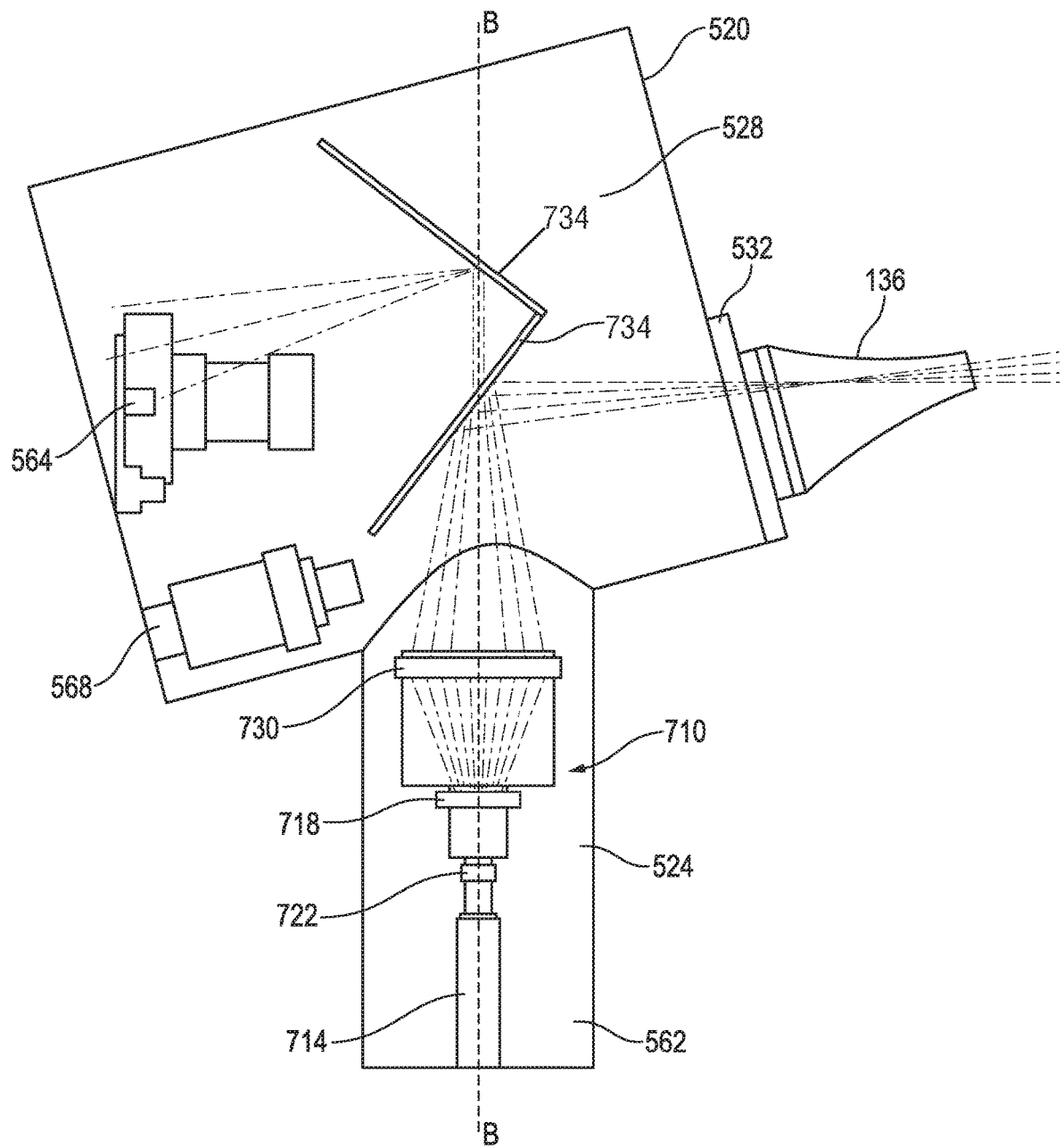
FIG. 15 illustrates a schematic view of a portion of the otoscope of FIG. 14.
Figure 16:
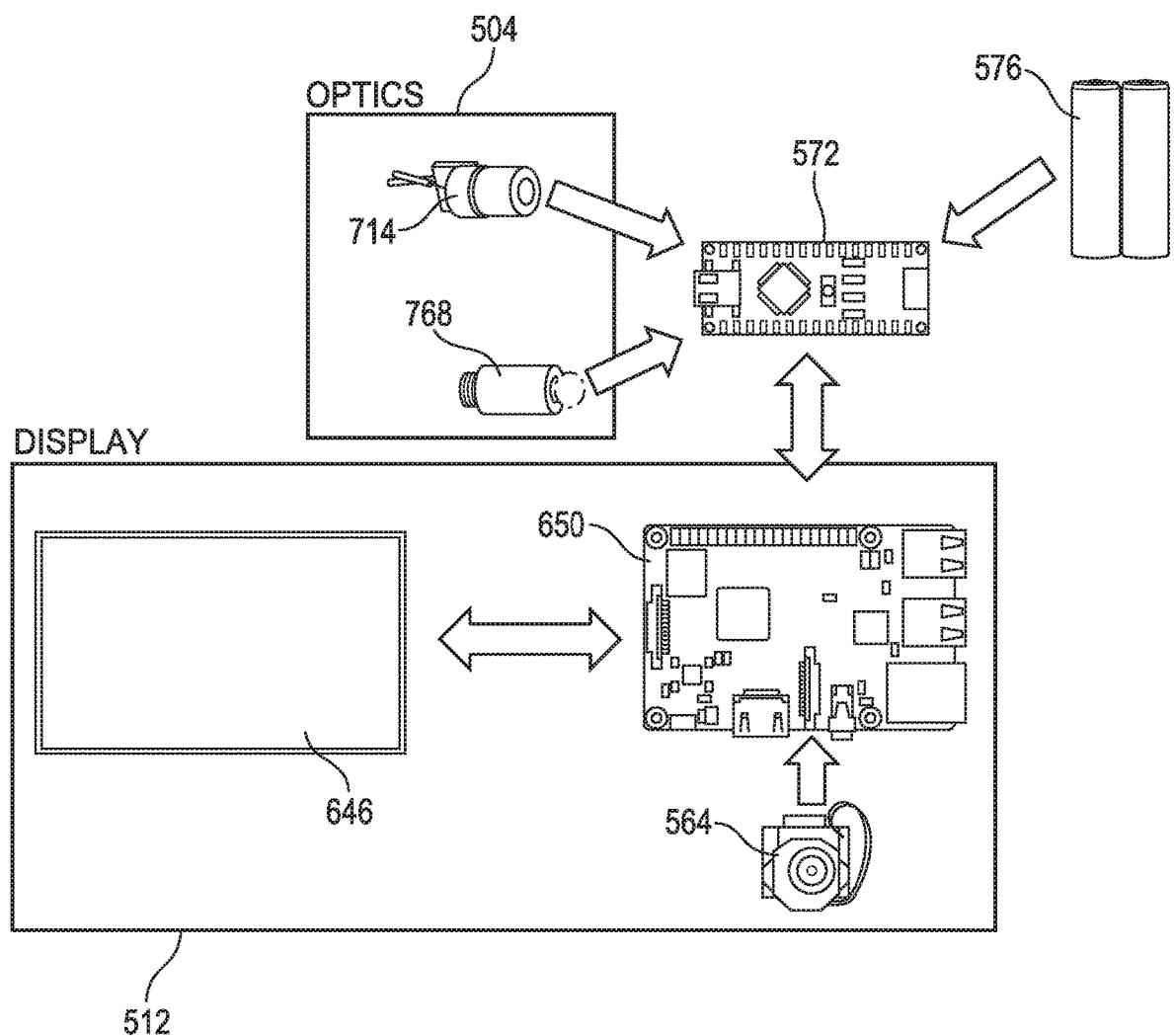
FIG. 16 is a schematic of the functionality of the otoscope of FIG. 14.
Figure 17:
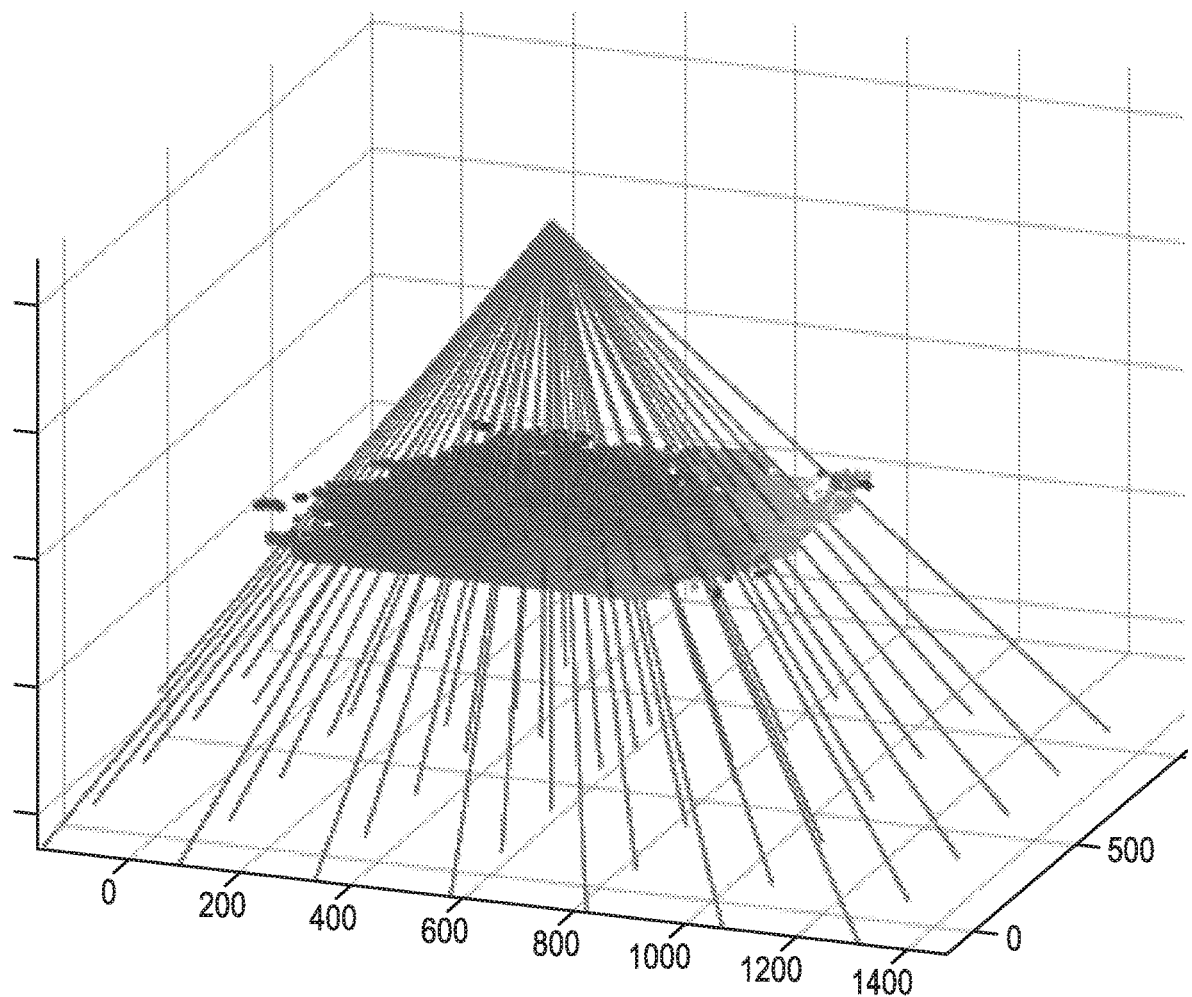
FIG. 17 shows an exemplary measurement of changes in distance between each dot of a grid array of dots and a focal point.

Another construction of the otoscope 500 is shown in FIGS. 14-19. The otoscope 500 of FIGS. 14-19 is similar to the otoscope 100 of FIGS. 1-13. Therefore, like reference numerals plus "400" will be used for like structure and only the differences discussed below. The otoscope 500 includes a housing 520 coupled to a handle 524. The housing 520 includes a longitudinal axis A (shown in FIG. 14) and encloses the camera 564 and the light 568 within the compartment 528. The housing 520 includes a mount 532 configured to removably receive and secure a speculum 136. The aperture 552 is in communication with the compartment 528 of the housing 520, aligns with the longitudinal axis A of the housing 520, and is configured to align with the outlet 148 of a standard speculum 136. The stimulus system of FIGS. 14-15 is a pneumatic bulb or insufflator bulb 1000 that is fluid communication with the housing 520 (and specifically the aperture 552) via a conduit or tube 1004. The healthcare provider can manually actuate (e.g., squeeze) the bulb 1000 to apply the stimulus (e.g. a pressure) through the housing 552 and the specula 136 to the tympanic membrane.

Further, with respect to 14 and 15, the handle 524 has a body 560 that defines a longitudinal axis B. The handle 524 includes a compartment 562 that supports the controller 572 (e.g., a microcontroller, such as a nano Arduino board), the microprocessor 650 (e.g., a Raspberry pi 3 B+, an application-specific integrated circuit (ASIC), another suitable electronic device), and a power source 576 (e.g., one or more replaceable 3.7 V batteries or one or more rechargeable batteries having any suitable voltage). As shown in FIG. 15, the compartment 528 of the housing 520 is in communication with the compartment 562 of the handle 524. The longitudinal axis A of the housing 520 is oriented at an obtuse angle (e.g., greater than 90-degree angle, FIG. 14) relative to the longitudinal axis B of the handle 524. The otoscope 500 also includes one or more physical actuators (e.g., buttons) coupled to the handle 524. In the illustrated construction, the otoscope 500 a start/stop record actuator 704. The handle 524 also includes a first projection 584 and a second projection 588 extending therefrom. The handle 524 is symmetrical about the longitudinal axis B when viewed from the rear (FIG. 3) such that the otoscope 500 is useable by both right-handed and left-handed healthcare providers. Additionally, the handle 524 is configured to be held comfortably by the healthcare provider.

With respect to FIG. 14, the otoscope 500 includes a display 512 having a screen assembly 630 that is movably (e.g., pivotably) coupled to the handle 524, as discussed above with respect to FIGS. 1-13. The display 512 is in communication with the components within the handle 524. The display 512 is in communication with the microprocessor 650. The screen 646 is capacitive and is constructed from a glass substrate that has a conductive coating (such as an indium tin oxide (ITO) coating) that is operable with surgical gloves. Like the screen 646 of FIGS. 1-13, the screen 646 may display a graphical user interface (GUI) that is a touch screen and may be configured to display one or more of the following: a battery life display, a true-color display of the tympanic membrane, an overlay display, a topographical display, a pressure of the ear canal, a pressure vs. time display, a color bar, file name, a save actuator, a view cycle actuator, and actuators corresponding, respectively, to fast forward, reverse, pause, and play. The "fast forward" actuator may instead by video speed actuator that allows the healthcare provider to pick a speed of the video, such as 0.25×, 0.5×, 0.75×, 1×, 1.25×, 1.5×, 1.75×, 2×, etc.

Further, with respect to FIG. 15, the optical components that are at least partially enclosed within handle 524 and include a laser assembly 710. The laser assembly 710 of FIGS. 14-19 includes a laser diode 714, a diffraction grating (DOE) 718, a plurality of lenses 722, 730, and a plurality of mirrors 734. A first lens 722 is a collimating lens and is positioned on a first side of the diffraction grating 718 and the second lens 730 is a convex lens positioned on a second, opposite side of the diffraction grating 718. The first lens 722 is positioned between the laser diode 714 and the diffraction grating 718. The laser diode 714, the diffraction grating 718, and the plurality of lenses 722, 730 are aligned along the longitudinal axis B of the handle 524. One of the plurality of mirrors 734 (e.g., a first or lower mirror 734) is positioned in the housing 520 and is oriented at a non-parallel and non-perpendicular angle to both the longitudinal axes A, B. One of the plurality of mirrors 734 (e.g., a second or upper mirror 734 is positioned within the housing and coupled to the first mirror 734 at an acute angle. When the light from the laser diode 714 passes through the diffraction grating 718, it is transformed from a single ray into a grid array of dots 738. The grid array of dots 738 is narrowed with the second lens 730 (e.g., converging lens) and then focused through the aperture 552 in the housing 520 and the outlet 148 of the speculum 136 with the first mirror 734 that is positioned within the housing 520. The second mirror 724 diverts light from the laser diode 714, which moves through the bottom mirror 734, away from the camera 564 because the camera 564 should only see the beams that reach the tympanic membrane. In other or additional constructions, other optical components besides a laser assembly are contemplated. In the illustrated construction, the laser diode 714 has a voltage ranging from 2.6V to 5V, a current rating of 50 mA, a power rating of 1 W, and a wavelength of 635 nm. The first lens 722 has a focal length of 6 mm. The diffraction grating is an 11×11 dot grid. The second lens 730 has a focal length of 1 in.

The light 568 is a light-emitting diode (LED), is positioned within the housing, and is configured to illuminate the ear canal and tympanic membrane but not to interfere with the laser assembly 710. The light 568 is configured to provide a stable output for a minimum of 30 seconds (for example) to provide consistent illumination to the ear canal. In other or additional constructions, other types of lights besides a LED are contemplated and the light 568 may be illuminated for less than or greater than 30 seconds.

Further, with respect to FIG. 5, the controller 572 is electrically coupled to and in communication with the light 568, the laser assembly 710, and the microprocessor 650. The microprocessor 650 is in in electrical communication with the controller 572 and includes a computer-readable memory (e.g., storage), a graphics card, a voltage regulator, a complementary metal-oxide-semiconductor (CMOS) circuit having a CMOS sensor, a battery charging circuit, a boost or step-up converter, and a gyroscopic sensor or accelerometer. The voltage regulator is in electrical communication with the batteries. The microprocessor 650 is configured to retrieve data from the memory and execute, among other things, software related to the processes and methods described herein. The memory includes a non-transitory, computer-readable storage medium. In one construction, the controller 572 includes memory having a storage capacity of 21.97 GB, and the graphics card includes memory having a storage capacity of 64 GB.

The microprocessor 650 of the otoscope 500 is configured to capture color video at a frequency of 22.5 Hz plus/minus 3 Hz (e.g., input frequency) and interlace it to 45 Hz plus/minus 6 Hz display format (e.g., output frequency). In one construction, the spatial resolution displayed is limited to the touch screen's 800×480 pixels, but the CMOS sensor 520 can switch its resolution between capturing 8-bit true-color display of 640×480 pixels at 90 Hz and 3-bit laser dot grid spatial measurement of 1920×1080 pixels at 30 Hz. The microprocessor 650 can process and output to the screen 646 the 8-bit true-color of the ear canal to the touch screen at 45 fps with a common baud rate of 9600 bps. In one construction, the average processing speed of the otoscope 500 is a minimum of 195.26 Mbps and the maximum processing speed is 221.18 Mbps. It is noted that as components improve through technological advances, processing speeds will increase and the otoscope described herein is not limited to the minimum or maximum processing speeds mentioned. The battery charging circuit regulates the backward voltage and/or current put into a battery during charging to ensure the batteries are not damaged. This circuit measure the battery charge level. The boost or step-up converter efficiently regulates the voltage from the batteries and increase the voltage to power higher voltage devices such as the computing unit. The gyroscopic sensor or accelerometer may be stored anywhere in the otoscope 500 to determine the device orientation over time and compare it with the video during processing and to flip the display (90° or 180°) if the healthcare provider inverts the device. The gyroscopic sensor or accelerometer determines screen orientation and stabilizes video. A pressure sensor measures the pressure stimulus applied to the tympanic membrane over time and it is stored in the body 560 of the otoscope 500, either in the handle 524 or in the housing 520.

Figure 19:
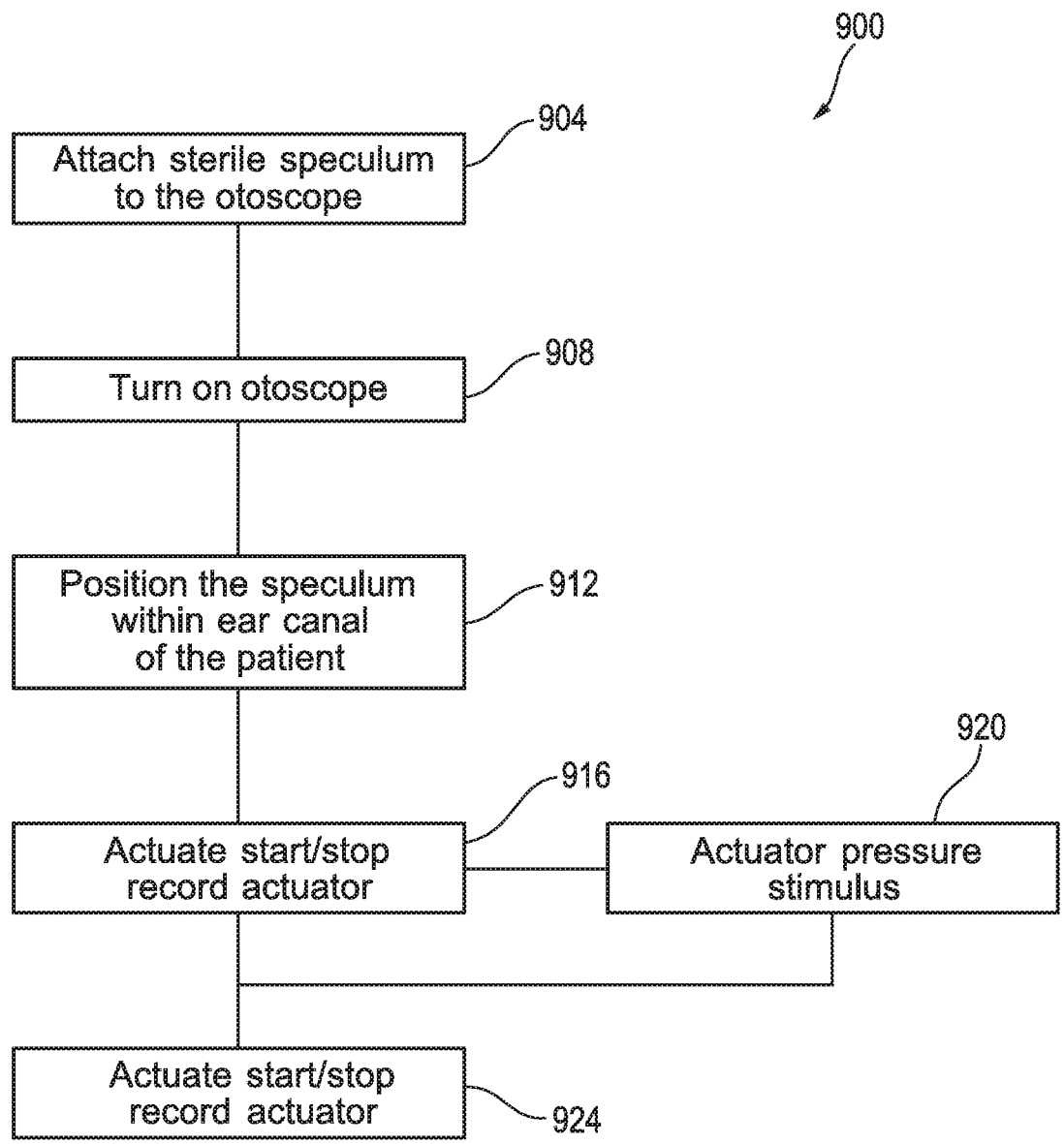
FIG. 19 shows a method of use of the otoscope of FIG. 14.

The flow chart in FIG. 19 illustrates a method 900 of use of the otoscope 500. At step 904, the healthcare provider attaches a sterile speculum 136 to the housing 520 of the otoscope 500. Then, at step 908, when the otoscope 500 is initially turned on, the camera 564 and the light 568 automatically turn on as well such that the activity of the tympanic membrane is also captured by the camera 564 and displayed in real-time on the screen 646. The healthcare provider can then position the speculum 136 within the ear canal of the patient, as step 912. At step 916, upon a first actuation of the start/stop record actuator 504, the microprocessor 650 begins to record the activity of the tympanic membrane and the laser assembly 710 is actuated to project the grid array 738 of dots onto the tympanic membrane. While the camera 564, at step 920, is recording, the healthcare provider can actuate the pneumatic bulb 1000 to apply a stimulus (e.g., pressure) to the tympanic membrane. This can be repeated one or more times. Accordingly, activity of the tympanic membrane and the changes to the grid array 738 of dots projected onto the tympanic membrane that are captured by the camera 564 can be stored by the microprocessor 650. At step 924, upon a second actuation of the start/stop record actuator 504, the microprocessor 650 stops recording the activity of the tympanic membrane and the laser assembly 710 is turned off. The second actuation of the start/stop actuator 504 will also initiate the processing of the entire duration of the video capture and will quickly lead to the looped video display of the diagnostic examination on the screen 546 of the otoscope 500. Also, the recorded and stored videos can later be exported or transferred (via USB, for example) such that the healthcare provider can re-watch and review the activity of the tympanic membrane later To process the video capture, the microprocessor 650 first assembles a trigonometric multiplication matrix based on a rectilinear matrix of the grid array 738 and an angle between the dots in the grid array 738. Because the angle between the dots in the grid array 738 is constant, a trigonometric algorithm is used to determine the distance from each dot to a focal point (FIG. 17) based on a distance of each dot to a central dot. The focal point is the last point at which both the laser rays converge and diverge, which in the illustrated embodiment inside the specula 136. The trigonometric multiplication matrix is used so that the distance of each laser dot to the center dot can be multiplied by the same grid location in the multiplication matrix to determine its distance with respect to the focal point. These distances can then be related to anything fixed in space with respect to the projected laser (e.g. specula tip). For ease of use, the trigonometric multiplication matrix is converted to arrays or vectors sorted, and then the arrays are based on distance from the center dot. The arrays are sorted from minimum distance from the center dot to maximum distance from the center dot. This is because the laser dot centers can be more easily be turned into an array sorted from minimum to maximum distance from the center than a rectilinear matrix. The statistical weight of each laser dot is also determined, so that if any dot is not detected in its position the other dots detected can be used to compensate for it in the average measure of displacement or position of a three-dimensional object in relation to anything fixed in relation to the measurement system.

The microprocessor 650 analyzes each image (e.g., still image or video) that is captured. For each frame, the microprocessor 650 operates as follows. Specifically, the microprocessor 650 determines the number of images that are saved. The microprocessor 650 imports the most recent video or videos, and determines the frame rate, image size, and color resolution. Additionally, the microprocessor 650 determines the frames with laser dots, removes image distortion caused by the lenses, crops frames with laser dots to remove noise, and determines x,y pixel position for the center of each dot. To determine the x,y pixel position for the center of each dot, the microprocessor 650 removes all color in the image that is not from the laser (e.g., filters for red if red laser is used) and filters for laser dots. Using color (e.g., red, green, blue, RGB), intensity can be determined based on how close the value is 255. The image under 50% of the max image is turned to black, and the brightest pixel is made equal to the maximum brightness. Based on diffraction the brightest dot should be the center dot for almost any normal shape regardless of distance. A statistical filter is applied to round out the data (e.g., a Gaussian filter), and the brightest pixel is made equal to the maximum brightness. Then, the center of each dot is found based on a regional maximum or peak analysis. Specifically, similar values are removed, peaks are grouped based on uniqueness within a tolerance value, and average pixel location is determined for each group. Once the x,y pixel position for each center dot is determined, the pixel distances of each laser dot center relative to the center dot is determined using the Pythagorean theorem. The dot positions are sorted from a minimum distance from the center dot to a maximum distance to the center dot to create an array of Pythagorean distance. A "z distance" is determined by multiplying the array of Pythagorean distance by the trigonometric multiple array. In other constructions, the z distance is collected based on the time it takes the light to hit the object and bounce back to the camera from each projected laser dot. This is known as time of flight or TOF. In another construction, the Z distance information is collected based on the wavelength shift of the light from each projected laser dot. This is known as LIDAR.

Videos representative of the tympanic membrane are configured to be output by the microprocessor 650 to the display 512. Specifically, the microprocessor 650 determines the maximum z distance and the minimum z distance for every frame. Then, the values are plotted with colors based on the z distance. For example, the respective z distances may be correlated to relative pressure (e.g., in mm/Pa) of the respective area or point on the tympanic membrane. That is, the color blue (and variations thereof) may represent 0 mm/Pa to 5 mm/pa, the color green (and variations thereof) may represent 5 mm/pa to 9 mm/Pa, the color yellow (and variations thereof) may represent 9 mm/Pa to 10 mm/Pa, the color orange (and variations thereof) may represent 10 mm/Pa to 12 mm/Pa, and the color red (and variations thereof) may represent above 12 mm/Pa. The plots are iterated frame by frame to assemble one or more videos.

Figure 18:
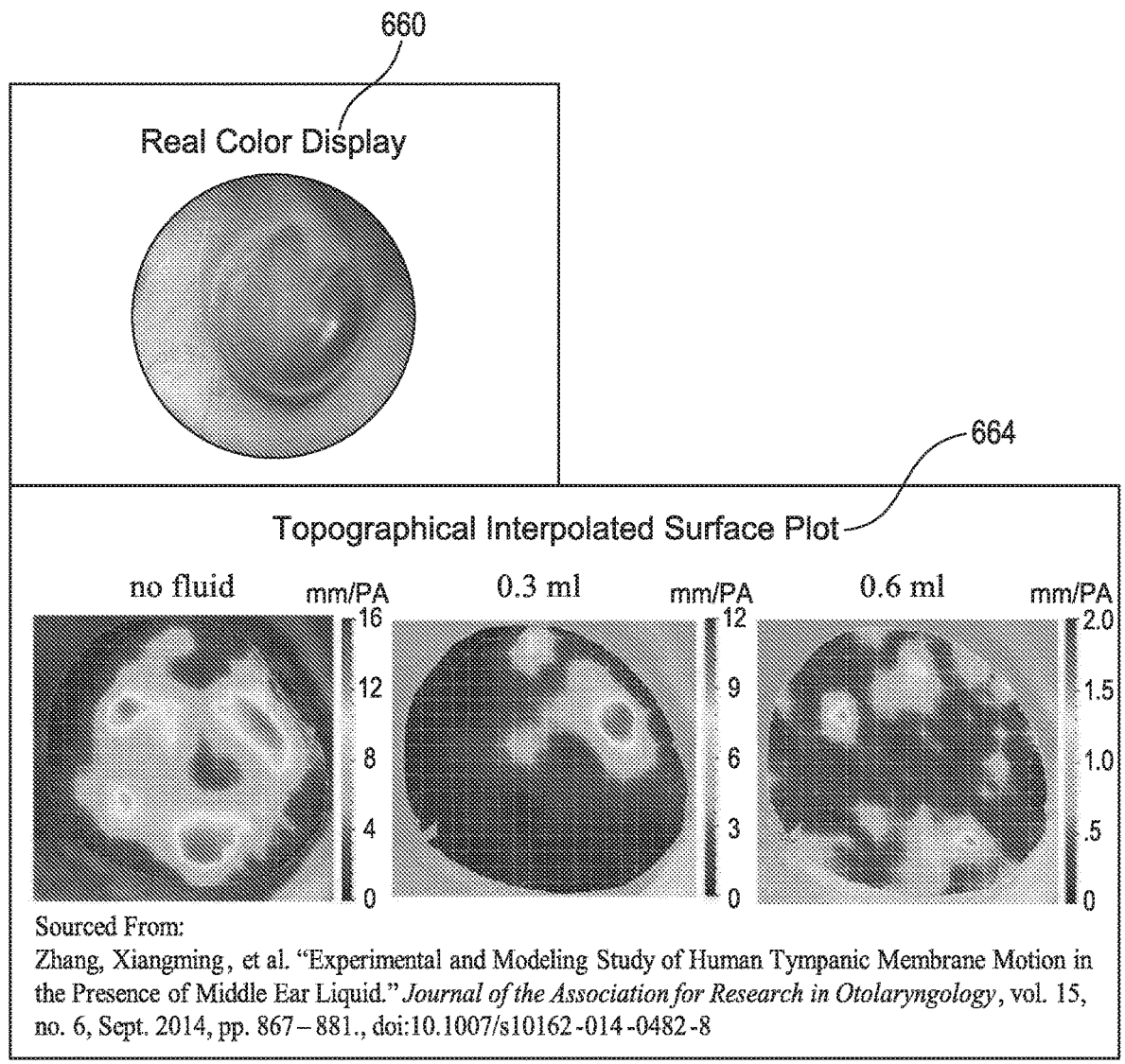
FIG. 18 show exemplary displays that are viewable by a healthcare provider on a graphical user interface of the otoscope of FIG. 14.

As shown in FIG. 18, the video of the activity of the tympanic membrane is viewable by the healthcare provider as a true-color display 660 and topographical display 664. The true-color display 660 shows no topographical information and illustrates the truest color of the ear canal possible by 8-bit color. The topographical display 664 is constructed by the microprocessor 650 using the z distances for each frame, discussed above. The topographical display 664 shows an interpolated two-dimensional ("2D") surface plot that shows only the colors. The topographical display 664 is associated with the color bar 666 indicating level display, which relates displacement of the tympanic membrane relative to measured dot displacement, pressure, or both measured dot displacement and pressure.

In another construction, the tympanic membrane is viewable by the healthcare provider as an overlay display. Similar to the topographical display 664, the overlay display is constructed by the microprocessor 650 using the z distances for each frame, discussed above. The overlay display is a combination of both the true-color and topographical information, where the topographical information is not interpolated (e.g., two-dimensional non-interpolated surface plot) and is instead represented with the grid array of dots, each having the appropriate color. The overlay display is also associated with the color bar 666 indicating level display, which relates displacement of the tympanic membrane relative to measured dot displacement, pressure, or both measured dot displacement and pressure.

As discussed above, the microprocessor 650 includes 195.26 Mbps of storage, which allows a healthcare provider to record the examination for a maximum of one minute per patient (e.g., there is enough storage for 1.46 GB per patient). In some constructions, the looped video displays may show a graphic 565 that is a plot that illustrates the relationship between maximal tympanic membrane deflection and the applied pressure. This graphic is positioned in the corner of the screen 646 so that it does not interfere with the visualization of the tympanic membrane. The healthcare provider can use actuators, similar to those of FIGS. 1-13, on the screen 646 to save videos to internal storage or delete them. Deleting the video will instantaneously clear the screen 646 and display the manufacturer's logo. In some constructions, the healthcare provider may also toggle between the real-time video feature and the record feature. In particular, when recording, the healthcare provider can press the start/stop record actuator 704 (after either saving or deleting the recording) to return to the real-time video feature. In the illustrated construction, this procedure can be repeated as many times as the clinician desires, but only one video will ever be stored on the device at a time. In other or additional constructions, multiple videos may be stored to the device, however.

Although the invention has been described in detail with reference to certain preferred constructions, variations and modifications exist within the scope and spirit of one or more independent aspects of the invention as described.

What is claimed is:

1. An otoscope comprising:
a handle;
a housing coupled to the handle and having an inlet;
a laser assembly at least partially enclosed within the handle and configured to selectively project, through the inlet, a grid array of dots on a tympanic membrane of a patient;
a camera supported by one of the handle or the housing and configured to selectively capture activity of the tympanic membrane;
a pressure transducer supported by one of the handle or the housing and configured to selectively apply a stimulus to the tympanic membrane;
a display pivotably coupled to the handle;
a controller in communication with laser assembly and the display; and
a microprocessor in communication with the controller, the camera, and the display,
wherein the display is configured to display the tympanic membrane in true color and a two-dimensional interpolated surface plot representing activity of the tympanic membrane in response to the stimulus.

2. The otoscope of claim 1, further comprising an actuator in communication with the microprocessor, wherein a first actuation of the actuator causes the microprocessor to record and a second actuation of the actuator causes the microprocessor to stop recording.

3. The otoscope of claim 1, wherein the pressure transducer is a manually-actuatable pneumatic bulb in fluid communication with the housing.

4. The otoscope of claim 1, wherein the display is configured to display real-time video and recorded video.

5. The otoscope of claim 1, wherein the laser assembly includes a laser diode, a diffraction grating, a first lens positioned on a first side of the diffraction grating, and second lens positioned on a second, opposite side of the diffraction grating, the first lens being positioned between the laser diode and the diffraction grating and being a collimating lens, the second lens being a convex lens.

6. The otoscope of claim 5, wherein the two-dimensional interpolated surface plot is a topographical surface plot having one or more colors, each of the one or more colors corresponding to a distance between a corresponding dot of the grid array of dots and a center dot of the grid array of dots.

7. The otoscope of claim 5, wherein the laser assembly is positioned in the handle and further including a mirror positioned within the housing, the mirror configured to redirect the grid array of dots from the laser assembly through the inlet.

8. An otoscope comprising:
a handle;
a housing coupled to the handle and having an inlet;
a laser assembly at least partially enclosed within the handle and configured to selectively project, through the inlet, a grid array of dots on a tympanic membrane of a patient, the laser assembly including a laser diode, a diffraction grating, a first lens positioned on a first side of the diffraction grating, and second lens positioned on a second, opposite side of the diffraction grating, the first lens being positioned between the laser diode and the diffraction grating and being a collimating lens, the second lens being a convex lens;
a camera supported by one of the handle or the housing and configured to selectively capture activity of the tympanic membrane;
a pressure transducer supported by one of the handle or the housing and configured to selectively apply a stimulus to the tympanic membrane;
a display supported by the handle;
a controller in communication with the laser assembly, and the display; and
a microprocessor in communication with the controller, the camera, and the display, the microprocessor configured to measure activity of the tympanic membrane in response to the stimulus applied by the pump based on the changes in distance between each dot of the grid array of dots projected on the tympanic membrane and a central dot of the grid array of dots and configured to construct a two-dimensional plot representing a distance of each dot relative to the center dot of the grid array of dots, wherein the microprocessor is configured to provide instructions to display the two-dimensional surface plot on the display.

9. The otoscope of claim 8, wherein the microprocessor is configured to construct a topographical surface plot from the two-dimensional surface plot, the topographical surface plot including a one or more colors, each of the one or more colors corresponding to a distance between a corresponding dot of the grid array of dots and the center dot of the grid array of dots.

10. The otoscope of claim 9, wherein the microprocessor is configured to display on the display a true-color display of the tympanic membrane and the topographical surface plot.

11. The otoscope of claim 8, wherein the pressure transducer is a manually-actuatable pneumatic bulb in fluid communication with the housing.

12. The otoscope of claim 8, wherein the display is configured to display real-time video and recorded video.

13. The otoscope of claim 8, further comprising an actuator in communication with the microprocessor, wherein a first actuation of the actuator causes the laser assembly to project the grid array of dots and the microprocessor to record and a second actuation of the actuator causes laser assembly to stop projecting the grid array of the dots and the microprocessor to stop recording.

14. The otoscope of claim 8, the laser assembly is positioned in the handle and further including a mirror positioned within the housing, the mirror configured to redirect the grid array of dots from the laser assembly through the inlet.

15. An otoscope comprising:
a handle;
a housing coupled to the handle and having an inlet;
a laser assembly at least partially enclosed within the handle and configured to selectively illuminate, through the inlet, a grid array of dots on a tympanic membrane of a patient;
a camera supported within the housing and configured to selectively capture activity of the tympanic membrane;
a pressure transducer supported by one of the handle or the housing and configured to selectively apply a stimulus to the tympanic membrane;
a display coupled to the handle;

a controller in communication with the laser assembly, the camera, and the display, the controller including a memory; and a microprocessor in communication with the controller and the display, wherein the microprocessor is configured to record a video of activity of the tympanic membrane;

wherein the display is configured to display real-time video and recorded video.

16. The otoscope of claim 15, wherein a laser diode, a diffraction grating, a first lens positioned on a first side of the diffraction grating, and second lens positioned on a second, opposite side of the diffraction grating, the first lens being positioned between the laser diode and the diffraction grating and being a collimating lens.

17. The otoscope of claim 15, further comprising an actuator in communication with the microprocessor, wherein a first actuation of the actuator causes the microprocessor to record and a second actuation causes the microprocessor to stop recording.

18. The otoscope of claim 17, wherein the display is configured to display a true-color display, a topographical display, and an overlay display.

19. The otoscope of claim 15, wherein the pressure transducer is a manually-actuatable pneumatic bulb in fluid communication with the housing.

20. The otoscope of claim 15, wherein the microprocessor is configured to measure the activity of the tympanic membrane in response to the stimulus applied by the pump based on the changes in distance between each dot of the grid array of dots projected on the tympanic membrane and a center dot of the grid array of dots and configured to construct a two-dimensional plot representing a distance of each dot relative to center dot of the grid array of dots.

21. A method of displaying activity of a tympanic membrane of a patient on a display of an otoscope:

activating a laser assembly of an otoscope to selectively project a grid array of dots on the tympanic membrane;

applying a stimulus to the tympanic membrane;

measuring, in response to the stimulus, changes in distance between each dot of the grid array of dots projected on the tympanic membrane and a center dot of the grid array of dots;

constructing a topographical surface plot from a two-dimensional surface plot; and displaying, on a display, the tympanic membrane and the topographical surface plot.

22. The method of claim 21, further comprising capturing activity of the tympanic membrane in real-time and displaying, on the display, captured real-time activity.

23. The method of claim 21, further comprising recording the response of the tympanic membrane to the stimulus.

* * * * *